United States Patent
Lee

(10) Patent No.: US 11,541,193 B2
(45) Date of Patent: Jan. 3, 2023

(54) METHOD FOR CONTROLLING TEMPERATURE OF HEATER OF AEROSOL GENERATION DEVICE FOR EACH INTERVAL AND AEROSOL GENERATION DEVICE FOR IMPLEMENTING SAME METHOD

(71) Applicant: KT&G CORPORATION, Daejeon (KR)

(72) Inventor: Jae Min Lee, Siheung-si (KR)

(73) Assignee: KT&G CORPORATION, Daejeon (KR)

( * ) Notice: Subject to any disclaimer, the term of this patent is extended or adjusted under 35 U.S.C. 154(b) by 157 days.

(21) Appl. No.: 16/959,293

(22) PCT Filed: Jul. 3, 2019

(86) PCT No.: PCT/KR2019/008101
§ 371 (c)(1),
(2) Date: Jun. 30, 2020

(87) PCT Pub. No.: WO2020/017789
PCT Pub. Date: Jan. 23, 2020

(65) Prior Publication Data
US 2021/0052835 A1    Feb. 25, 2021

(30) Foreign Application Priority Data
Jul. 18, 2018 (KR) .................. 10-2018-0083656

(51) Int. Cl.
*A24F 47/00* (2020.01)
*A61M 15/06* (2006.01)
(Continued)

(52) U.S. Cl.
CPC ............... *A61M 15/06* (2013.01); *H05B 1/02* (2013.01); *A24B 15/167* (2016.11); *A24F 40/57* (2020.01);
(Continued)

(58) Field of Classification Search
CPC .................. A24F 40/50; H05B 1/02
(Continued)

(56) References Cited

U.S. PATENT DOCUMENTS 10,111,465 B2 * 10/2018 Liu .................. A24F 40/40
10,470,496 B2    11/2019 Bernauer et al.
(Continued)

FOREIGN PATENT DOCUMENTS

CN    104662160 A    5/2015
CN    105027016 A    11/2015
(Continued)

OTHER PUBLICATIONS

Korean Office Action for 10-2018-0083656 dated Nov. 4, 2019.
(Continued)

*Primary Examiner* — Neil Abrams
(74) *Attorney, Agent, or Firm* — Sughrue Mion, PLLC

(57) ABSTRACT

Provided is an aerosol generating device including a heater configured to generate an aerosol by heating an aerosol generating substance; and a controller configured to control power supplied to the heater, wherein the controller distinguishes a first section, a second section, and a third section and controls power supplied to the heater, and calculates a control reference ratio by using at least two from among the first section, the second section, and the third section and controls power supplied to the heater based on the calculated control reference ratio.

16 Claims, 19 Drawing Sheets

(51) Int. Cl.
*H05B 1/02* (2006.01)
*A24B 15/167* (2020.01)
*A24F 40/57* (2020.01)

(52) U.S. Cl.
CPC .............. *A61M 2205/8206* (2013.01); *H05B 2203/021* (2013.01)

(58) Field of Classification Search
USPC .......................................................... 131/328
See application file for complete search history.

(56) References Cited

U.S. PATENT DOCUMENTS

| | | | |
|---|---|---|---|
| 2013/0340750 A1* | 12/2013 | Thorens | A24F 40/50 128/202.21 |
| 2014/0299125 A1 | 10/2014 | Buchberger | |
| 2015/0208727 A1 | 7/2015 | Kuczaj | |
| 2015/0237916 A1 | 8/2015 | Farine et al. | |
| 2017/0196273 A1 | 7/2017 | Qiu | |

FOREIGN PATENT DOCUMENTS

| | | |
|---|---|---|
| CN | 105636466 A | 6/2016 |
| CN | 107407941 A | 11/2017 |
| IN | 9123/CHENP/2012 | 4/2014 |
| JP | H06-67737 A | 3/1994 |
| JP | H09258601 A | 10/1997 |
| JP | 2015-13192 A | 1/2015 |
| KR | 10-2014-0063506 A | 5/2014 |
| KR | 10-2014-0094513 A | 7/2014 |
| KR | 10-2015-0084779 A | 7/2015 |
| KR | 10-2015-0102924 A | 9/2015 |
| KR | 10-2017-0107518 A | 9/2017 |
| KR | 10-2017-0137066 A | 12/2017 |
| WO | 2011/148881 A1 | 12/2011 |
| WO | 2012/109371 A2 | 8/2012 |
| WO | 2016/166064 A1 | 10/2016 |
| WO | 2017/205692 A1 | 11/2017 |

OTHER PUBLICATIONS

International Search Report for PCT/KR2019/008101 dated, Oct. 1, 2019 (PCT/ISA/210).
Extended European Search Report dated Feb. 3, 2022 in European Application No. 19837702.0.
First Office Action issued in the China National Intellectual Property Administration dated Oct. 28, 2022 in corresponding Chinese Application No. 201980006657.X.

* cited by examiner

METHOD FOR CONTROLLING TEMPERATURE OF HEATER OF AEROSOL GENERATION DEVICE FOR EACH INTERVAL AND AEROSOL GENERATION DEVICE FOR IMPLEMENTING SAME METHOD

CROSS REFERENCE TO RELATED APPLICATIONS

This application is a National Stage of International Application No. PCT/KR2019/008101 filed Jul. 3, 2019, claiming priority based on Korean Patent Application No. 10-2018-0083656, filed Jul. 18, 2018.

TECHNICAL FIELD

The disclosure relates to a method of controlling the temperature of a heater of an aerosol generating device for each section and an aerosol generating device for implementing the method, and more particularly, to a method of quickly generating a sufficient amount of aerosol to be inhaled by a user by dividing the temperature of a heater of an aerosol generating device into sections and rapidly heating the heater, and an aerosol generating device for implementing the method.

BACKGROUND ART

Recently, there has been increasing demand for alternative ways of overcoming the disadvantages of traditional cigarettes. For example, there is growing demand for a method of generating aerosol by heating an aerosol generating material in cigarettes, rather than by combusting cigarettes. Accordingly, research into a heating-type cigarette or a heating-type aerosol generator has been actively conducted.

An aerosol-generating device generally includes a heater that generates an aerosol by heating an aerosol-generating substrate, and, in order to control the heater, a separate main controller unit (MCU) is provided to control the temperature of the heater through proportional integral difference (PID) control. When an MCU controls the temperature of a heater through PID control, no overshoot occurs until the temperature of the heater reaches a target temperature for generating aerosol due to the feedback algorithm of the PID control. However, it takes a long time to heat the heater, and thus a large amount of battery power is consumed and a user has to wait for a long time.

DESCRIPTION OF EMBODIMENTS

Technical Problem

The disclosure provides a method of quickly generating a sufficient amount of aerosol to be inhaled by a user through a rapid pre-heating and an aerosol generating device for implementing the method.

Solution to Problem

According to an aspect of the disclosure, an aerosol generating device includes a heater configured to generate an aerosol by heating an aerosol generating substance; and a controller configured to control power supplied to the heater, wherein the controller controls the power supplied to the heater differently in a first section, a second section, and a third section and control power supplied to the heater, and calculates a control reference ratio based on at least two from among the first section, the second section, and the third section and controls power supplied to the heater based on the calculated control reference ratio.

According to another aspect of the disclosure, a method of controlling power supplied to a heater, the method includes a first stage of controlling the heater to be heated below a predetermined target temperature; a second stage of lowering the temperature of the heater when the temperature of the heater exceeds the target temperature; and a third stage of maintaining the temperature of the heater at the target temperature, wherein, in the second stage and the third stage, power supplied to the heater is controlled based on a control reference ratio calculated based on at least two from among a duration of the first stage, a duration of the second stage, and a duration of the third stage.

According to one or more embodiments, there is provided a computer-readable recording medium having recorded thereon a computer program for implementing the method.

Advantageous Effects of Disclosure

According to the disclosure, a user may enjoy inhalation of aerosol through an aerosol generating device quickly without waiting for a long time until a heater of the aerosol generating device is sufficiently heated.

BEST MODE

Figure 1:
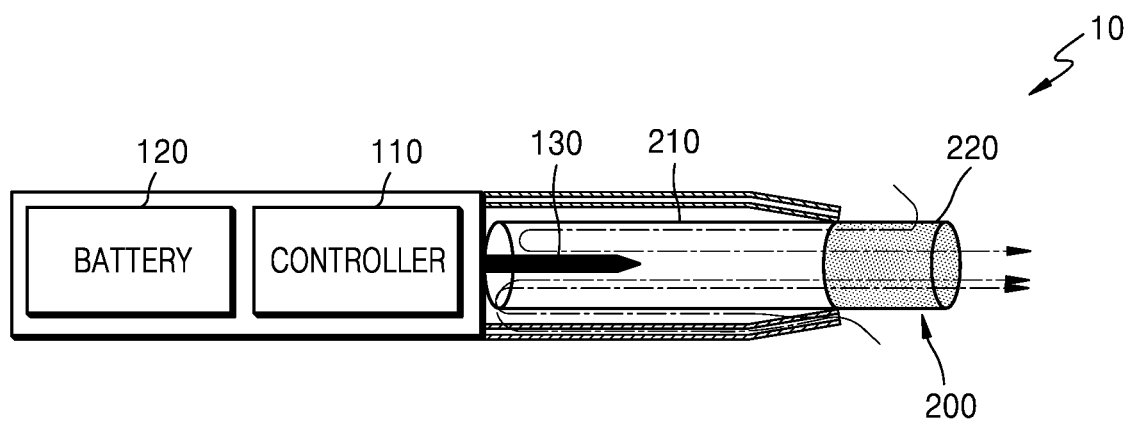
FIGS. 1 to 3 are diagrams showing examples in which a cigarette is inserted into an aerosol generator.

According to an aspect of the disclosure, an aerosol generating device includes a heater configured to generate an aerosol by heating an aerosol generating substance; and a controller configured to control power supplied to the heater, wherein the controller is further configured to: control the power supplied to the heater differently in a first section, a second section, and a third section, calculate a control reference ratio based on at least two sections from among the first section, the second section, and the third section, and control the power supplied to the heater based on the calculated control reference ratio.

The controller may control the power supplied to the heater based on comparison between the calculated control reference ratio with a preset comparison control value.

The controller may calculate the control reference ratio based on a duration of the second section.

The controller may calculate the control reference ratio based on a sum of a duration of the first section and a duration of the second section divided by a duration of the third section.

The calculated control reference ratio may be smaller than 1.

The calculated control reference ratio may be ratio of a duration of the second section to a duration of the third section.

The calculated control reference ratio may be smaller than 1.

The calculated control reference ratio may be a ratio of a duration of the first section to a duration of the second section.

The calculated control reference ratio may be smaller than 2.

The controller may perform a pulse width modulation (PWM) control according to an output state of a battery in the first section, and perform a proportional integral differential (PID) control in the second section and the third section.

According to another aspect of the disclosure, a method of controlling power supplied to a heater, the method includes a first stage of controlling the heater to be heated below a predetermined target temperature; a second stage of controlling to lower the temperature of the heater when the temperature of the heater exceeds the target temperature; and a third stage of maintaining the temperature of the heater at the target temperature, wherein, in the second stage and the third stage, power supplied to the heater is controlled based on a control reference ratio calculated based on at least two from among a duration of the first stage, a duration of the second stage, and a duration of the third stage.

In the second stage and the third stage, power supplied to the heater may be controlled based on a result of comparing the calculated control reference ratio with a preset comparison control value.

In the second stage and the third stage, the control reference ratio is calculated based on a duration of the second stage.

In the third stage, the control reference ratio may be calculated by dividing a sum of the duration of the first stage and the duration of the second stage by the duration of the third stage.

The calculated control reference ratio may be smaller than 1.

The calculated control reference ratio may be a ratio of the duration of the second stage to the duration of the third stage.

The calculated control reference ratio may be smaller than 1.

The calculated control reference ratio may be a ratio of the duration of the first stage to the duration of the second stage.

The calculated control reference ratio may be smaller than 2.

According to another aspect of the disclosure, there is provided a computer-readable recording medium having recorded thereon a computer program for implementing the method.

MODE OF DISCLOSURE

As the present disclosure allows for various changes and numerous embodiments, particular embodiments will be illustrated in the drawings and described in detail in the written description. The attached drawings for illustrating one or more embodiments are referred to in order to gain a sufficient understanding, the merits thereof, and the objectives accomplished by the implementation. However, the embodiments may have different forms and should not be construed as being limited to the descriptions set forth herein.

The example embodiments will be described below in more detail with reference to the accompanying drawings. Those components that are the same or are in correspondence are rendered the same reference numeral regardless of the figure number, and redundant explanations are omitted.

While such terms as "first," "second," etc., may be used to describe various components, such components are not be limited to the above terms. The above terms are used only to distinguish one component from another.

An expression used in the singular encompasses the expression of the plural, unless it has a clearly different meaning in the context.

In the present specification, it is to be understood that the terms "including," "having," and "comprising" are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

When a certain embodiment may be implemented differently, a specific process order may be performed differently from the described order. For example, two consecutively described processes may be performed substantially at the same time or performed in an order opposite to the described order.

Hereinafter, embodiments of the present disclosure will be described in detail with reference to the drawings.

Figure 2:
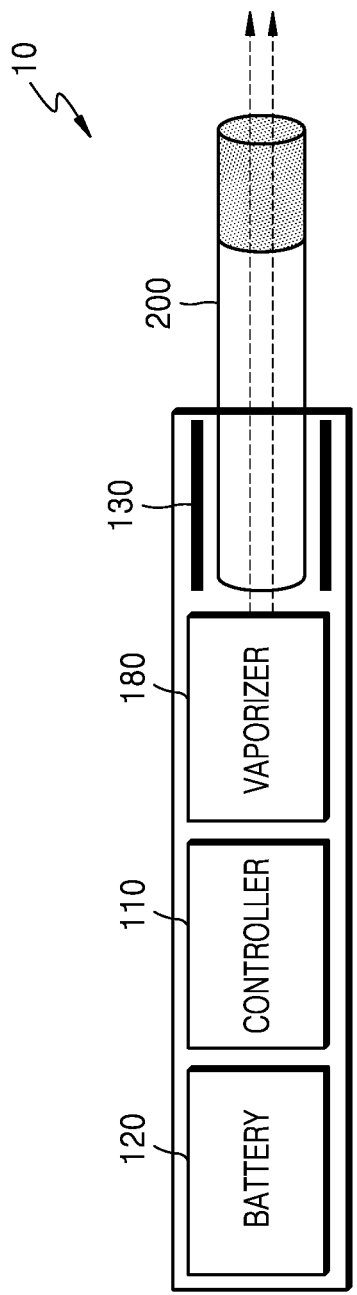
Figure 3:
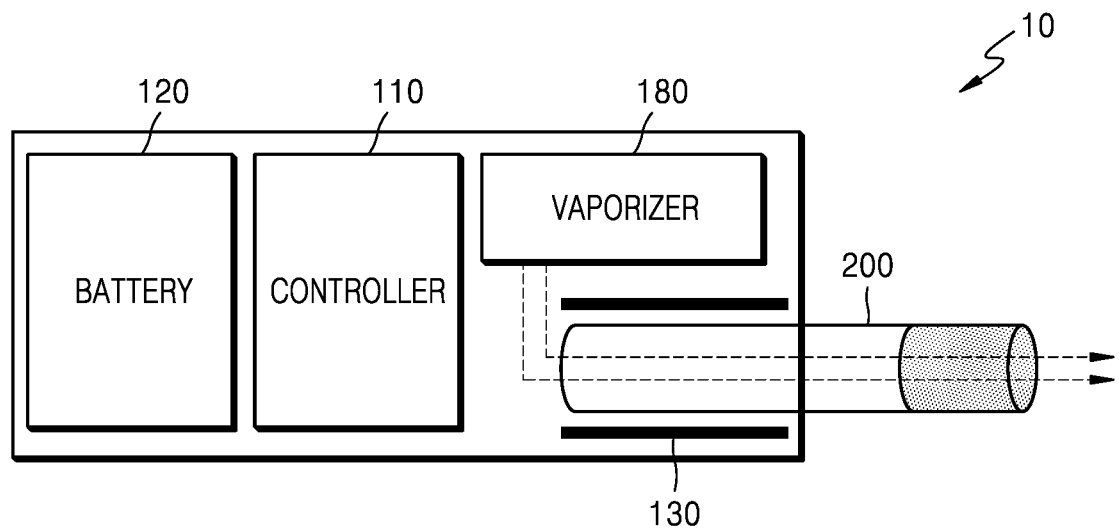

FIGS. 1 to 3 are diagrams showing examples in which a cigarette is inserted into an aerosol generator.

Referring to FIG. 1, an aerosol generator 10 includes a battery 120, a controller 110, and a heater 130. Referring to FIG. 2 and FIG. 3, the aerosol generator 10 further includes a vaporizer 180. Also, a cigarette 200 may be inserted into an inner space of the aerosol generator 10.

The elements related to the embodiment are illustrated in the aerosol generator 10 of FIGS. 1 to 3. Therefore, one of ordinary skill in the art would appreciate that other universal elements than the elements shown in FIGS. 1 to 3 may be further included in the aerosol generator 10.

Also, FIGS. 2 and 3 show that the aerosol generator 10 includes the heater 130, but if necessary, the heater 130 may be omitted.

In FIG. 1, the battery 120, the controller 110, and the heater 130 are arranged in a row. Also, FIG. 2 shows that the battery 120, the controller 110, the vaporizer 180, and the heater 130 are arranged in a row. Also, FIG. 3 shows that the vaporizer 180 and the heater 130 are arranged in parallel. However, an internal structure of the aerosol generator 10 is not limited to the examples shown in FIGS. 1 to 3. That is, according to a design of the aerosol generator 10, arrangement of the battery 120, the controller 110, the heater 130, and the vaporizer 180 may be changed.

When the cigarette 200 is inserted into the aerosol generator 10, the aerosol generator 10 operates the heater 130 and/or the vaporizer 180 to generate aerosol from the cigarette 200 and/or the vaporizer 180. The aerosol generated by the heater 130 and/or the vaporizer 180 may be transferred to a user via the cigarette 200.

As necessary, even when the cigarette 200 is not inserted in the aerosol generator 10, the aerosol generator 10 may heat the heater 130.

The battery 120 supplies the electric power used to operate the aerosol generator 10. For example, the battery 120 may supply power for heating the heater 130 or the vaporizer 180 and supply power for operating the controller 110. In addition, the battery 120 may supply power for operating a display, a sensor, a motor, and the like installed in the aerosol generator 10.

The controller 120 controls the overall operation of the aerosol generator 10. In detail, the controller 110 may control operations of other elements included in the aerosol generator 10, as well as the battery 120, the heater 130, and the vaporizer 180. Also, the controller 110 may check the status of each component in the aerosol generator 10 to determine whether the aerosol generator 10 is in an operable state.

The controller 110 includes at least one processor. A processor can be implemented as an array of a plurality of logic gates or can be implemented as a combination of a general-purpose microprocessor and a memory in which a program executable in the microprocessor is stored. It will be understood by one of ordinary skill in the art that the present disclosure may be implemented in other forms of hardware.

The heater 130 may be heated by the electric power supplied from the battery 120. For example, when the cigarette 200 is inserted in the aerosol generator 10, the heater 130 may be located outside the cigarette 200. Therefore, the heated heater 130 may raise the temperature of an aerosol generating material in the cigarette.

The heater 130 may be an electro-resistive heater. For example, the heater 130 includes an electrically conductive track, and the heater 130 may be heated as a current flows through the electrically conductive track. However, the heater 130 is not limited to the above example, and any type of heater may be used provided that the heater is capable of being heated to a desired temperature. Here, the desired temperature may be set in advance on the aerosol generator 10, or may be set by a user.

In addition, in another example, the heater 130 may include an induction heating type heater. In detail, the heater 130 may include an electrically conductive coil for heating the cigarette 200 in an induction heating method, and the cigarette may include a susceptor that may be heated by the induction heating type heater.

For example, the heater may include a tubular type heating element, a plate type heating element, a needle type heating element, or a rod type heating element, and may heat the inside or outside of the cigarette 200 according to the shape of the heating element.

Also, there may be a plurality of heaters 130 in the aerosol generator 10. Here, the plurality of heaters 130 may be arranged to be inserted into the cigarette 200 or on the outside of the cigarette 200. Also, some of the plurality of heaters 130 may be arranged to be inserted into the cigarette 200 and the other may be arranged on the outside of the cigarette 200. In addition, the shape of the heater 130 is not limited to the example shown in FIGS. 1 to 3, but may be manufactured in various shapes.

The vaporizer 180 may generate aerosol by heating a liquid composition and the generated aerosol may be delivered to the user after passing through the cigarette 200. In other words, the aerosol generated by the vaporizer 180 may move along an air flow passage of the aerosol generator 10, and the air flow passage may be configured for the aerosol generated by the vaporizer 180 to be delivered to the user through the cigarette 200.

For example, the vaporizer 180 may include a liquid storage unit, a liquid delivering unit, and a heating element, but is not limited thereto. For example, the liquid storage unit, the liquid delivering unit, and the heating element may be included in the aerosol generator 10 as independent modules.

The liquid storage may store a liquid composition. For example, the liquid composition may be a liquid including a tobacco containing material including a volatile tobacco flavor component, or a liquid including a non-tobacco material. The liquid storage unit may be detachable from the vaporizer 180 or may be integrally manufactured with the vaporizer 180.

For example, the liquid composition may include water, solvents, ethanol, plant extracts, flavorings, flavoring agents, or vitamin mixtures. The flavoring may include, but is not limited to, menthol, peppermint, spearmint oil, various fruit flavoring ingredients, etc. The flavoring agent may include components that may provide the user with various flavors or tastes. Vitamin mixtures may be a mixture of at least one of vitamin A, vitamin B, vitamin C, and vitamin E, but are not limited thereto. Also, the liquid composition may include an aerosol former such as glycerin and propylene glycol.

The liquid delivery element may deliver the liquid composition of the liquid storage to the heating element. For example, the liquid delivery element may be a wick such as cotton fiber, ceramic fiber, glass fiber, or porous ceramic, but is not limited thereto.

The heating element is an element for heating the liquid composition delivered by the liquid delivering unit. For example, the heating element may be a metal heating wire, a metal hot plate, a ceramic heater, or the like, but is not limited thereto. In addition, the heating element may include a conductive filament such as nichrome wire and may be positioned as being wound around the liquid delivery element. The heating element may be heated by a current supply and may transfer heat to the liquid composition in contact with the heating element, thereby heating the liquid composition. As a result, aerosol may be generated.

For example, the vaporizer 180 may be referred to as a cartomizer or an atomizer, but is not limited thereto.

In addition, the aerosol generator 10 may further include universal elements, in addition to the battery 120, the controller 110, the heater 130, and the vaporizer 180. For example, the aerosol generator 10 may include a display capable of outputting visual information and/or a motor for outputting tactile information. In addition, the aerosol generator 10 may include at least one sensor (a puff sensor, a temperature sensor, a cigarette insertion sensor, etc.) Also, the aerosol generator 10 may be manufactured to have a structure, in which external air may be introduced or internal air may be discharged even in a state where the cigarette 200 is inserted.

Although not shown in FIGS. 1 to 3, the aerosol generator 10 may configure a system with an additional cradle. For example, the cradle may be used to charge the battery 120 of the aerosol generator 10. Alternatively, the heater 130 may be heated while the cradle and the aerosol generator 10 are coupled to each other.

The cigarette 200 may be similar to a traditional combustive cigarette. For example, the cigarette 200 may include a first portion containing an aerosol generating material and a second portion including a filter and the like. The second portion of the cigarette 200 may also include the aerosol generating material. For example, an aerosol generating material made in the form of granules or capsules may be inserted into the second portion.

The entire first portion may be inserted into the aerosol generator 10 and the second portion may be exposed to the outside. Alternatively, only a portion of the first portion may be inserted into the aerosol generator 10 or the entire first portion and a portion of the second portion may be inserted into the aerosol generator 10. The user may puff aerosol while holding the second portion by the mouth of the user. At this time, the aerosol is generated as the outside air passes through the first portion, and the generated aerosol passes through the second portion and is delivered to a user's mouth.

For example, the outside air may be introduced through at least one air passage formed in the aerosol generator 10. For example, opening and closing of the air passage formed in the aerosol generator 10 and/or the size of the air passage may be adjusted by a user. Accordingly, the amount and smoothness of smoke may be adjusted by the user. In another example, the outside air may be introduced into the cigarette 200 through at least one hole formed in a surface of the cigarette 200.

Hereinafter, an example of the cigarette 200 will be described with reference to FIG. 4.

Figure 4:
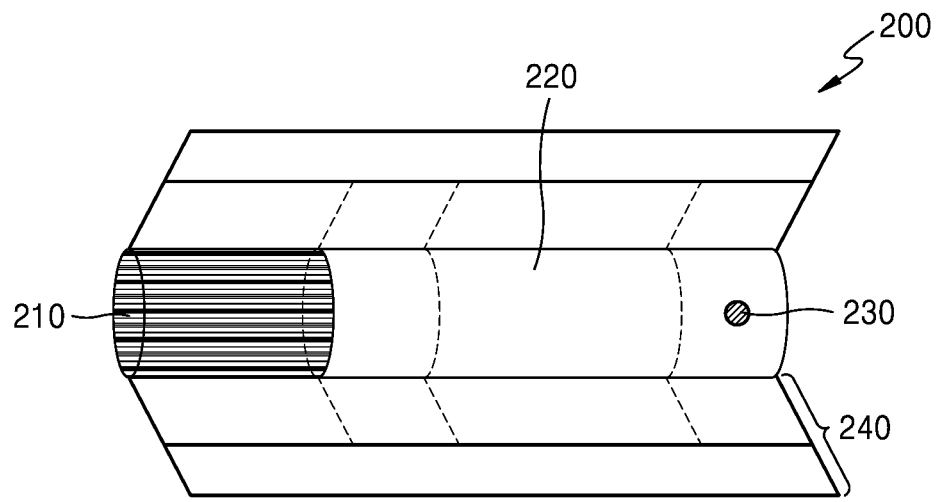
FIG. 4 illustrates an example of a cigarette.

FIG. 4 illustrates an example of a cigarette.

Referring to FIG. 4, the cigarette 200 includes a tobacco rod 210 and a filter rod 220. The first portion described above with reference to FIGS. 1 to 3 may include the tobacco rod 210 and the second portion may include the filter rod 220.

In FIG. 4, the filter rod 220 is shown as a single segment, but is not limited thereto. In other words, the filter rod 220 may include a plurality of segments. For example, the filter rod 220 may include a first segment for cooling down the aerosol and a second segment for filtering a predetermined component included in the aerosol. Also, if necessary, the filter rod 220 may further include at least one segment performing other functions.

The cigarette 200 may be packaged by at least one wrapper 240. The wrapper 240 may include at least one hole through which the outside air is introduced or inside air is discharged. For example, the cigarette 200 may be packaged by one wrapper 240. In another example, the cigarette 200 may be packaged by two or more wrappers 240. For example, the tobacco rod 210 may be packaged by a first wrapper and the filter rod 220 may be packaged by a second wrapper. In addition, the tobacco rod 210 and the filter 220 that are respectively packaged by single wrappers, and then, the cigarette 200 may be entirely re-packaged by a third wrapper. When each of the tobacco rod 210 and the filter rod 220 includes a plurality of segments, each of the segments may be packaged by a single wrapper, and the segments of the cigarette 200 may be re-packaged by another wrapper.

The tobacco rod 210 includes an aerosol generating material. For example, the aerosol generating material may include at least one of glycerin, propylene glycol, ethylene glycol, dipropylene glycol, diethylene glycol, triethylene glycol, tetraethylene glycol, and oleyl alcohol, but it is not limited thereto. In addition, the tobacco rod 210 may include other additive materials like a flavoring agent, a wetting agent, and/or an organic acid. Also, a flavoring liquid such as menthol, humectant, etc. may be added to the tobacco rod 210 by being sprayed to the tobacco rod 210.

The tobacco rod 210 may be manufactured variously. For example, the tobacco rod 210 may be fabricated as a sheet or a strand. Also, the tobacco rod 210 may be fabricated by tobacco leaves that are obtained by fine-cutting a tobacco sheet. Also, the tobacco rod 210 may be surrounded by a heat conducting material. For example, the heat-conducting material may be, but is not limited to, a metal foil such as aluminum foil. For example, the heat conducting material surrounding the tobacco rod 210 may improve a thermal conductivity applied to the tobacco rod by evenly dispersing the heat transferred to the tobacco rod 210, and thereby improving tobacco taste. Also, the heat conducting material surrounding the tobacco rod 210 may function as a susceptor that is heated by an inducting heating type heater. Although not shown in the drawings, the tobacco rod 210 may further include a susceptor, in addition to the heat conducting material surrounding the outside thereof.

The filter rod 220 may be a cellulose acetate filter. In addition, the filter rod 220 is not limited to a particular shape. For example, the filter rod 220 may be a cylinder type rod or a tube type rod including a cavity therein. Also, the filter rod 220 may be a recess type rod. When the filter rod 220 includes a plurality of segments, at least one of the plurality of segments may have a different shape from the others.

The filter rod 220 may be manufactured to generate flavor. For example, a flavoring liquid may be sprayed to the filter rod 220 or separate fibers on which the flavoring liquid is applied may be inserted in the filter rod 220.

Also, the filter rod 220 may include at least one capsule 230. Here, the capsule 230 may generate flavor or may generate aerosol. For example, the capsule 230 may have a structure, in which a liquid containing a flavoring material is wrapped with a film. The capsule 230 may have a circular or cylindrical shape, but is not limited thereto.

When the filter rod 220 includes a segment for cooling down the aerosol, the cooling segment may include a polymer material or a biodegradable polymer material. For example, the cooling segment may include pure polylactic acid alone, but the material for forming the cooling segment is not limited thereto. In some embodiments, the cooling segment may include a cellulose acetate filter having a plurality of holes. However, the cooling segment is not limited to the above examples, and may include any material that is capable of cooling down the aerosol.

Although not shown in FIG. 4, the cigarette 200 according to the embodiment may further include a front-end filter. The front-end filter may be positioned at a side of the tobacco rod 210, the side not facing the filter rod 220. The front-end filter may prevent the tobacco rod 210 from escaping to outside, and may prevent the liquefied aerosol from flowing to the aerosol generator 10 (see FIGS. 1 to 3) from the tobacco rod 210 during smoking.

Figure 5:
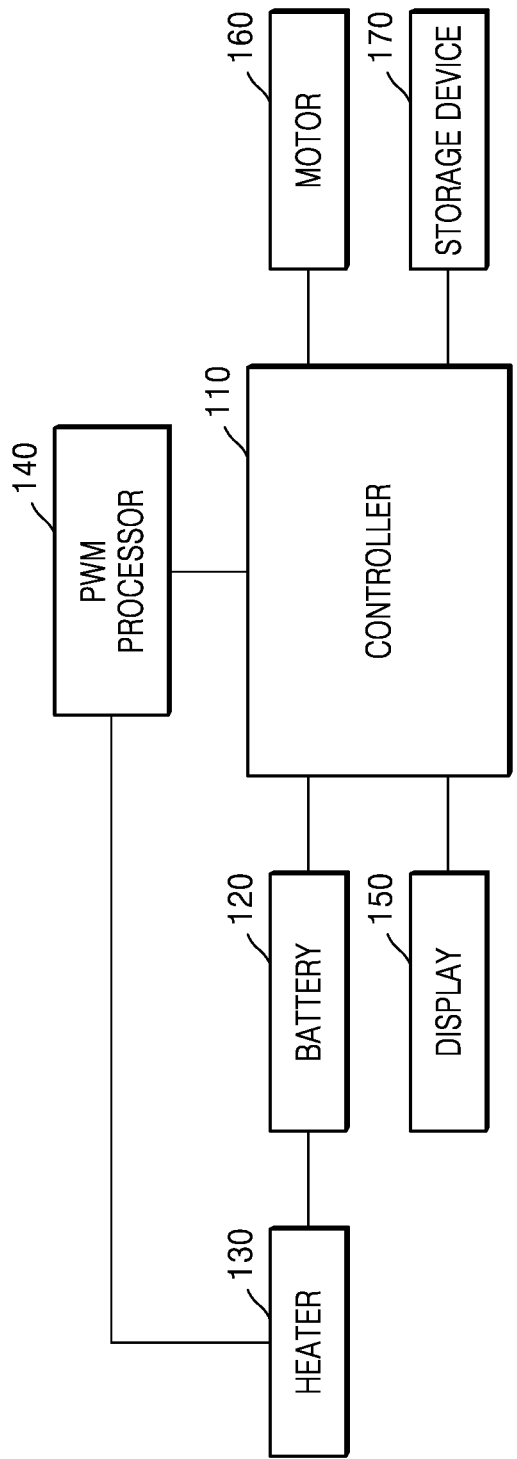
FIG. 5 is a block diagram of an example of an aerosol generator according to an embodiment of the disclosure.

FIG. 5 is a block diagram of an example of the aerosol generator 10 according to an embodiment of the disclosure.

Referring to FIG. 5, the aerosol generator 10 according to the embodiment includes the controller 110, the battery 120, the heater 130, a pulse-width modulation processor 140, a display 150, a motor 160, and a storage device 170.

The controller 110 controls overall operations of the battery 120, the heater 130, the pulse-width modulation processor 140, the display 150, the motor 160, and the storage device 170 included in the aerosol generator 10. Although not shown in FIG. 5, in some embodiments, the controller 110 may further include an input receiver (not shown) for receiving a button input or a touch input from a user and a communicator (not shown) that may communicate with an external communication device such as a user terminal. Although not shown in FIG. 5, the controller 110 may further include a module for performing proportional integral difference (PID) control on the heater 130.

The battery 120 supplies electric power to the heater 130, and the magnitude of the electric power supplied to the heater 130 may be adjusted by the controller 110.

The heater 130 generates heat due to specific resistance when receiving the electric power. When an aerosol generating material is in contact with (coupled to) the heated heater, the aerosol may be generated.

The pulse-width modulation processor 140 may allow the controller 110 to control the electric power supplied to the heater 130 by transferring a pulse-width modulation (PWM) signal to the heater 130. In some embodiments, the pulse-width modulation processor 140 may be included in the controller 110.

The display 150 visually outputs various alarm messages of the aerosol generator 10 to allow the user of the aerosol generator 10 to check the messages. The user may check a low-battery message, an overheat alarm message of the heater, etc. output on the display 150, and may take measures before the aerosol generator 10 stops operating or is damaged.

The motor 160 is driven by the controller 110 and allows the user to recognize that the aerosol generator 10 is ready for use through a tactile response.

The storage device 170 may store various information by which the controller 110 appropriately controls the electric power supplied to the heater 130 and various flavors are provided to the user of the aerosol generator 10. For example, a first method or a second method that will be described later may be one of methods for controlling the electric power supplied to the heater 130 by the controller 110, and may be stored in the storage device 170 and then transferred to the controller 110 by fetch of the controller 110. In another example, the information stored in the storage device 170 may include a temperature profile that is referred to by the controller 110 for controlling the temperature of the heater to be appropriately reduced or increased according to lapse of time, a controller reserve ratio that will be described later, a comparing control value, etc., and the information may be sent to the controller 110 according to a request from the controller 110. The storage device 170 may include a non-volatile memory such as a flash memory, or may include a volatile memory that temporarily stores data only during being conducted in order to ensure fast data input/output (I/O) speed.

The method for the controller 110 to control the electric power supplied to the heater 130 according to the embodiment will be described later with reference to FIG. 6 for convenience of description.

Figure 6:
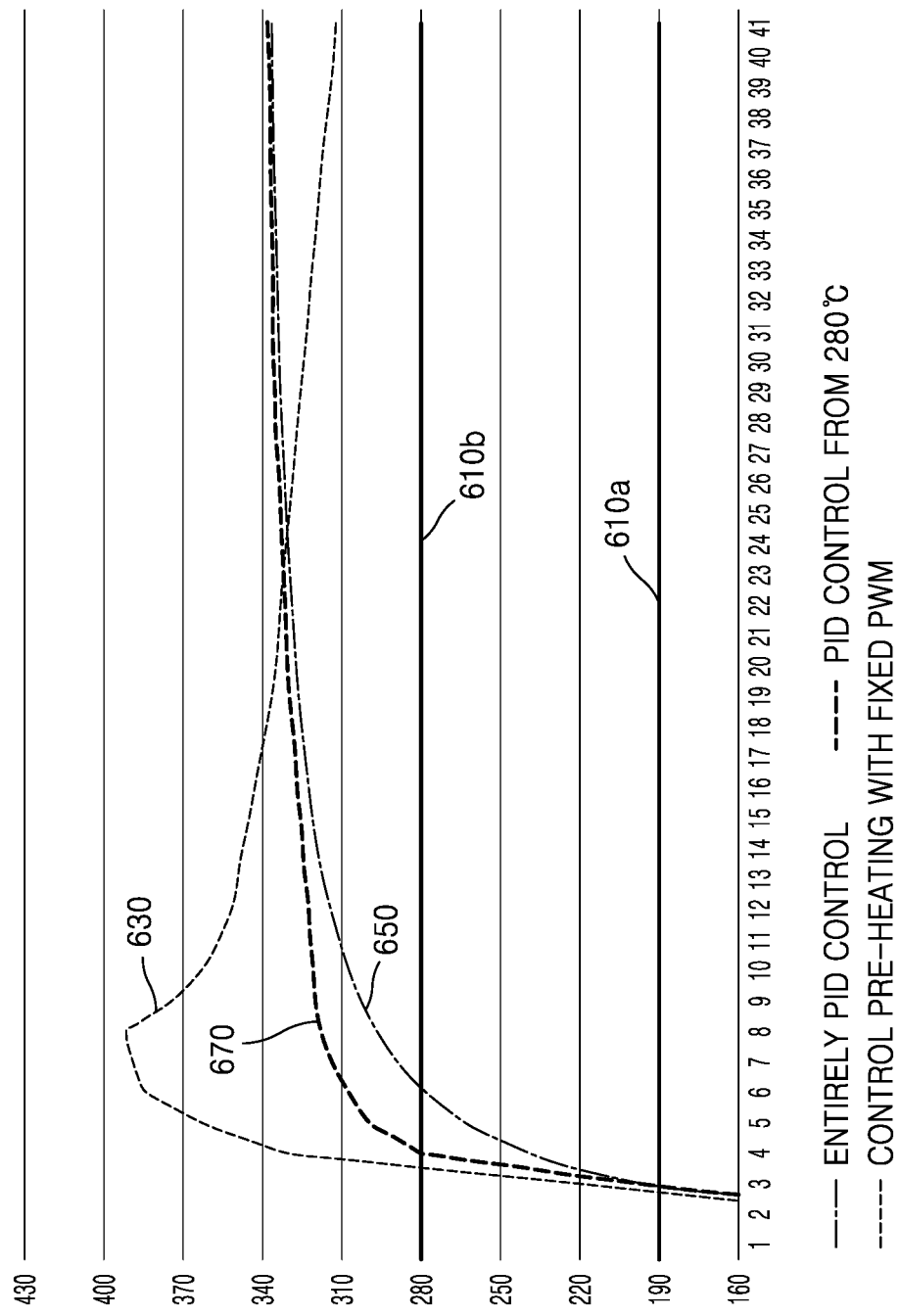
FIG. 6 is a graph illustrating a method of controlling a temperature of a heater in an aerosol generator according to sections.

FIG. 6 is a graph illustrating a method of controlling a temperature of a heater in an aerosol generator according to sections.

Referring to FIG. 6, the graph includes boundary lines 610a and 610b representing a pre-heating temperature section, a temperature variation curve 630 of a heater according to a PWM method according to the related art, a temperature variation curve 650 of the heater according to the PID method according to the related art, and a temperature variation curve 670 of the heater according to the embodiment. In FIG. 6, a transverse axis denotes time in seconds and a longitudinal axis denotes Celsius temperature.

The boundary lines 610a and 610b representing the pre-heating temperature section respectively denote a lower limit and an upper limit of the pre-heating temperature section according to the disclosure. Referring to FIG. 6, the lower limit of the pre-heating temperature section is 190° C. and the upper limit of the pre-heating temperature section is 280° C. Since the temperatures 190° C. and 280° C. are examples according to the embodiment of the disclosure, the lower limit and the upper limit of the pre-heating temperature section may vary depending on embodiments. For example, the lower limit of the pre-heating temperature section is selected from a range of 160° C. to 220° C. and the upper limit of the pre-heating temperature section may be selected from a range of 250° C. to 310° C.

According to the temperature variation curve 630 of the heater according to the PWM method of the related art, the temperature of the heater rapidly rises to about 390° C. after 7 or 8 seconds later, and slowly decreases. When the electric power is supplied to the heater with a fixed PWM, an overshoot may occur after the temperature of the heater reaches the target temperature.

In addition, according to the temperature variation curve 650 of the heater according to the PID method of the related art, the temperature of the heater slowly increases and the overshoot does not occur. However, it takes longer for the temperature of the heater to reach the target temperature, e.g., 340° C., as compared with other control methods.

According to the temperature variation curve 670 of the heater according to the embodiment, a pre-heating speed may be faster than the PID method and at the same time, the overshoot does not occur which may occur when the electric power supplied to the heater is controlled by the fixed PWM control method.

Hereinafter, operations of the aerosol generator for controlling the temperature of the heater for each section according to the exemplary embodiment will be described in detail with reference to FIGS. 5 and 6.

The controller 110 controls the temperature of the heater 130 differently in a pre-heating temperature section and a temperature maintaining section.

The controller 110 controls the electric power supplied to the heater 130 by using the first method in the pre-heating temperature section. In detail, the controller 110 controls the electric power supplied to the heater 130 by the first method until the temperature of the heater reaches the upper limit of the pre-heating temperature section.

In some embodiments, the controller 110 may control the electric power supplied to the heater by the first method until the temperature of the heater reaches the upper limit from the lower limit of the pre-heating temperature section. According to the embodiment, a starting point where the controller 110 starts to control the heater by the first method is restricted to the lower limit of the pre-heating temperature section, and thus, the time when the controller 110 starts to control the electric power supplied to the heater by the first method becomes clear. The pre-heating temperature section is a temperature range including the lower limit and the upper limit, and referring to FIG. 6, the lower limit of the pre-heating temperature section may be 190° C. and the upper limit of the pre-heating temperature section may be 280° C. In some embodiments, the lower limit and the upper limit of the pre-heating temperature section may have other values than the above examples, e.g., 190° C. and 280° C.

Here, the first method may be a PWM control method with a fixed output.

In an alternative embodiment, the controller 110 may check an output voltage range of the battery 120 and may heat the temperature to the upper limit of the pre-heating temperature section according to an upper limit of the output voltage range. Since the output voltage range of the battery 120 varies depending on malfunction or a charged amount, the controller 110 checks the output voltage range of the battery 120 and heats the heater as fast as possible according to the upper limit of the output voltage range, and thus faster pre-heating speed may be ensured as compared with the heater control method according to the related art.

On sensing that the temperature of the heater reaches the upper limit of the pre-heating temperature section, the controller 110 controls the electric power supplied to the heater by the second method until the temperature of the heater reaches the target temperature from the upper limit of the pre-heating temperature section.

Here, the target temperature is a temperature necessary for the heater in direct/indirect contact with the aerosol generating material to generate aerosol. The target temperature may be higher than the upper limit of the pre-heating temperature section. Referring to FIG. 6, the target temperature may be 340° C. In some embodiments, the target temperature may be lower or higher than 340° C.

The second method is distinguished from the first method, and is a method of controlling the electric power supplied to the heater. For example, when the first method is the PWM control method, the second method may be the PID control method. The controller 110 may receive the temperature profile and the PID control instructions stored in the storage device 170, and after that, may execute the PID control so that the temperature of the heater, which has rapidly increased to the upper limit of the pre-heating temperature section, may reach the target temperature at a relatively slow speed. In detail, the controller 110 may appropriately adjust gains of a proportional term, an integral term, and a derivative term in order to increase the temperature of the heater to the target temperature without generating overshoot of the heater.

The storage device 170 stores various information for performing the PID control. The various information stored in the storage device 170 may include a logic or algorithm for calculating an appropriate gain when the heater reaches a certain temperature at a certain time, as well as exemplary values of the gains of the proportional term, the integral term, and the derivative term for performing the PID control.

The controller 110 may determine that the temperature of the heater reaches the upper limit of the pre-heating temperature section by using a temperature sensor or a timer. The controller 110 may determine that the temperature of the heater reaches the upper limit of the pre-heating temperature section by reading a value of a temperature sensor connected to the heater.

Also, the controller 110 measures the time taken to control the electric power supplied to the heater by the first method by using a timer built in or connected thereto through wires, and when the controller 110 senses the elapse of time that is predicted as the time when the temperature of the heater reaches the upper limit based on the measurement result, the controller 110 may change the method of controlling the electric power supplied to the heater from the first method to the second method. For example, when the first method is the fixed PWM control method and the heater is a resistor a resistivity of which is well known, the controller 110 may calculate the temperature of the heater, which rises in proportion to an amount of power supplied to the heater. Thus, the controller 110 may calculate the time taken for the temperature of the heater to reach the upper limit of the pre-heating temperature section from a current temperature of the heater.

In an alternative embodiment, the controller 110 may control the electric power supplied to the heater by the second method until the temperature of the heater reaches the target temperature from the upper limit of the pre-heating temperature section, based on a ratio of the upper limit of the pre-heating temperature section with respect to the target temperature, which is set in advance. For example, when the ratio of the upper limit of the pre-heating temperature section with respect to the target temperature (hereinafter, referred to as "control reference ratio") is 0.8 and the upper limit of the pre-heating temperature section is 240° C., the controller 110 may control the electric power supplied to the heater by the second method until the temperature of the heater becomes 300° C. from 240° C. Here, setting of the control reference ratio as 0.8 is an example according to the embodiment of the disclosure, and thus, the control reference ratio may vary according to the embodiment, and the upper limit of the pre-heating temperature section, e.g., 240° C., may also vary. For example, the control reference ratio may be in the range of 0.65 to 0.95.

$$T_2 = T_3 - a * \left(\frac{T_3}{10}\right) \qquad \text{[Equation 1]}$$

Equation 1 above is an example used when the controller 110 determines a time point for changing the controlling method from the first method to the second method. In Equation 1, T2 denotes a temperature of the heater when the controller 110 starts to control the electric power supplied to the heater by the second method, that is, the upper limit of the pre-heating temperature section. T3 denotes a target temperature of the heater, and "a" denotes a proportional coefficient within a range of 1.5 to 2.5.

In Equation 1, "a" varies according to a control signal transmission cycle of the controller 110 transmitting a power control signal to the heater. The value of "a" is experimentally determined and increases in proportion to the control signal transmission cycle. In addition, the variable "a" corresponding to each control signal transmission cycle is stored in the form of a table and may be called by the controller 110 to be used to calculate T2.

When it is assumed that the controller 110 transmits the power control signal to the heater at an interval of 10 milliseconds (ms) and controls the electric power supplied to the heater in the fixed PWM control method for fast pre-heating speed of the heater, overshoot of about 10% with respect to the target temperature occurs experimentally. As an example, when the power control signal in the PWM control method is transmitted to a heater having a target temperature of 300° C. at an interval of 10 ms, an overshoot occurs and a maximum temperature of the overshoot is 330° C. Therefore, in order to prevent the overshoot of the heater, the controller 110 needs to change the power control method with respect to the heater before the heater reaches the target temperature.

For example, when the proportional coefficient "a" is determined to be 2 when the interval at which the controller 110 transmits the power control signal to the heater is 10 ms and the target temperature of the heater is 300° C., the controller 110 changes the power control method when the temperature of the heater reaches 240° C., according to Equation 1. Since the proportional coefficient "a" increases in proportion to the control signal transmission cycle, if the control signal transmission cycle increases in this case, the temperature of the heater at the time when the controller 110 changes the power control method from the first method to the second method would become lower than 240° C. In another example, if the proportional coefficient is 2.5 and the control signal transmission cycle is 100 ms, the controller 110 may change the power control method of the heater from the first method to the second method at the temperature of 225° C.

As described above, according to the disclosure, the controller 110 controls the electric power supplied to the heater by the first method, changes the power control method to the second method when the temperature of the heater reaches the upper limit of the pre-heating temperature section, and then, performs the power control on the heater to the target temperature. Therefore, faster pre-heating speed than that of the related art may be ensured, and thus, a sufficient amount of aerosol may be rapidly provided to the user. Moreover, since the overshoot of the heater may be prevented, unpleasant smoking experience of the user caused due to carbonization of a medium (aerosol generating material) may be prevented in advance.

In particular, since the power control method with respect to the heater is changed from the first method to the second method, taking into account the transmission cycle of the power control signal transmitted from the controller 110 to the heater and the target temperature at the same time as expressed by Equation 1, the controller included in the aerosol generator according to the exemplary embodiments may exactly determine the time point for maximizing the benefits of the fast pre-heating speed and prevention of the overshoot.

Figure 7:
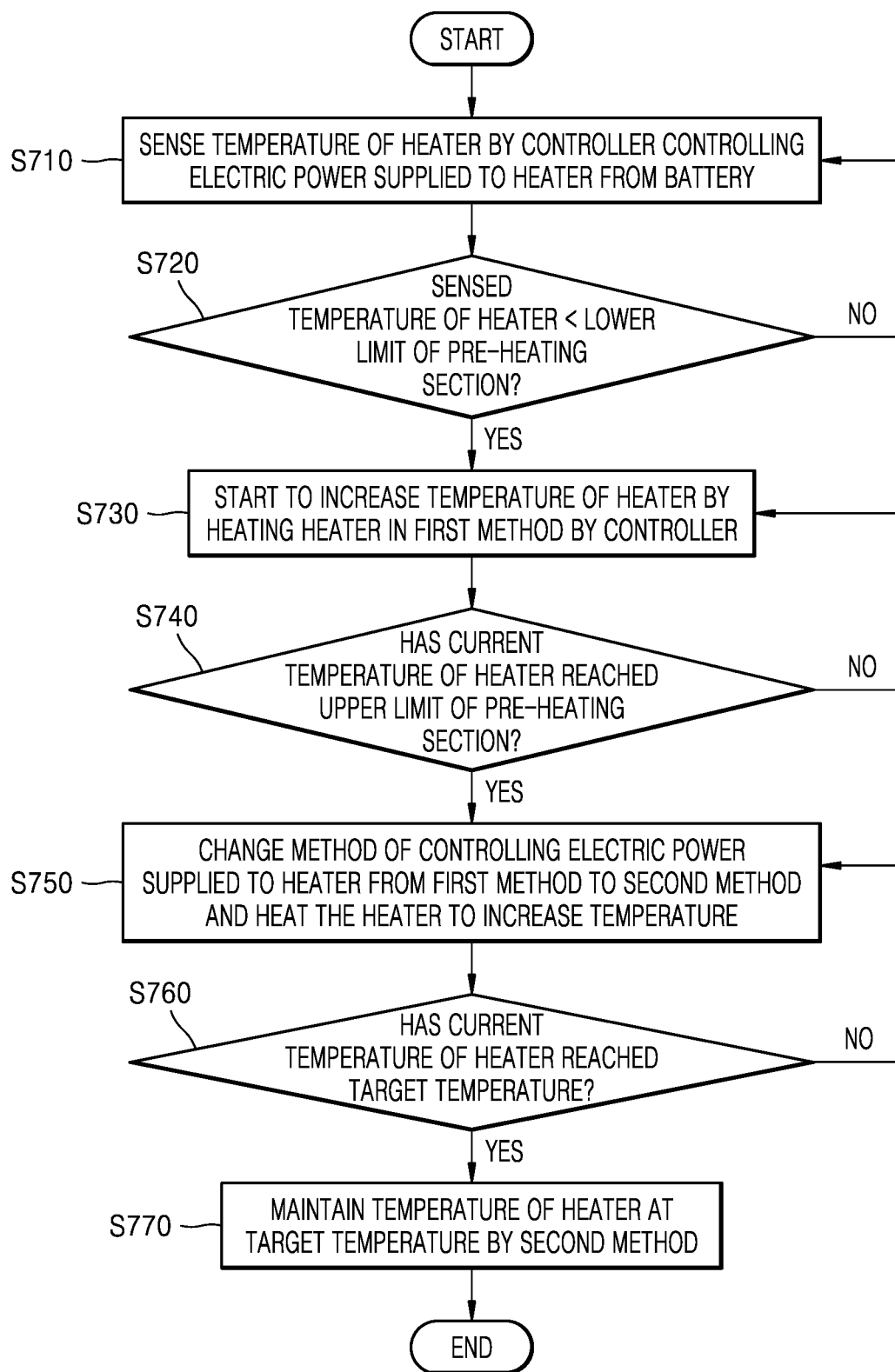
FIG. 7 is a flowchart illustrating an example of a method of controlling electric power supplied to a heater according to an embodiment of the disclosure.

FIG. 7 is a flowchart illustrating an example of a method of controlling electric power supplied to a heater according to an embodiment of the disclosure.

Since the method illustrated with reference to FIG. 7 may be implemented by the aerosol generator 10 of FIG. 5, descriptions below will be provided with reference to FIG. 5 and descriptions that are already described above with reference to FIGS. 5 and 6 are omitted.

When the battery 120 starts to supply electric power to the heater 130, the controller 110 regularly checks the temperature of the heater 130 (S710).

The controller 110 determines whether the temperature of the heater 130 is lower than the lower limit of the pre-heating section (S720), and when the temperature of the heater 130 is lower than the lower limit of the pre-heating section, the controller 110 starts to raise the temperature of the heater 130 by heating the heater 130 by the first method (S730).

According to the embodiment, operations S710 and S720 may be omitted, and in this case, the controller 110 controls the electric power supplied to the heater 130 by the first method from the time when the heater 130 starts to be heated.

After operation S730, the controller 110 determines whether the current temperature of the heater 130 has reached the upper limit of the pre-heating section (S740). When the current temperature of the heater 130 has reached the upper limit of the pre-heating section, the controller 110 changes the control method of the electric power supplied to the heater 130 from the first method to the second method and controls the heater 130 to be continuously heated (S750). As described above, in operation S750, the first method may be the PWM control method with a fixed output and the second method may be the PID control method.

The controller 110 checks whether the current temperature of the heater 130 has reached the target temperature (S760), and when the current temperature of the heater 130 has reached the target temperature, the controller 110 controls the temperature of the heater 130 to be maintained at the target temperature by the second method (S770).

Figure 8:
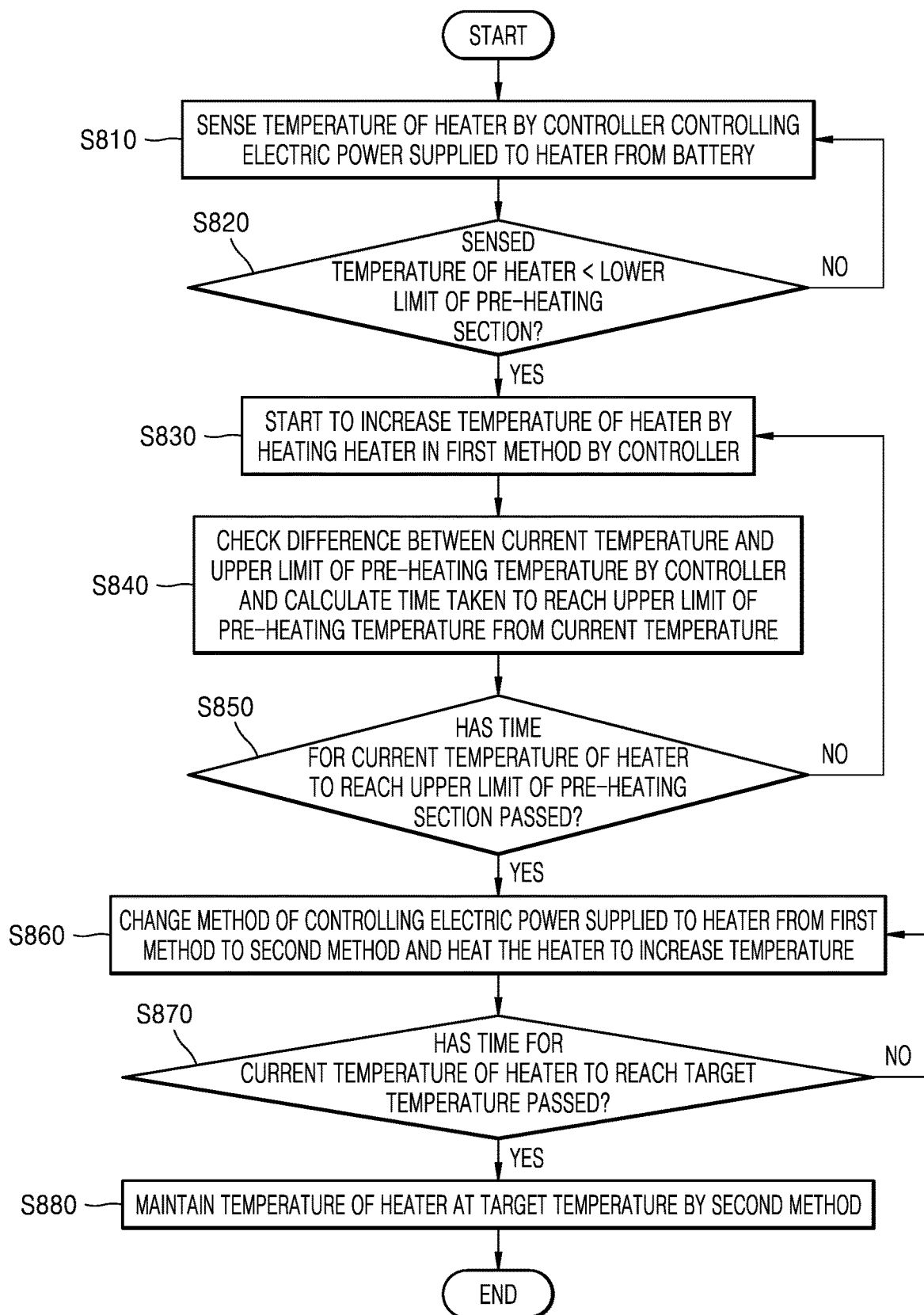
FIG. 8 is a flowchart illustrating an example of a method of controlling electric power supplied to a heater according to another embodiment of the disclosure.

FIG. 8 is a flowchart illustrating an example of a method of controlling electric power supplied to a heater according to another embodiment of the disclosure.

Since the method illustrated with reference to FIG. 8 may be implemented by the aerosol generator 10 of FIG. 5, descriptions below will be provided with reference to FIG. 5 and descriptions that are already described above with reference to FIGS. 5 and 6 are omitted. FIG. 8 is a flowchart illustrating an alternative embodiment, in which the controller 110 determines the power control method of the heater based on a timer, not a temperature sensor.

When the battery 120 starts to supply electric power to the heater 130, the controller 110 regularly checks the temperature of the heater 130 (S810).

The controller 110 determines whether the temperature of the heater 130 is lower than the lower limit of the pre-heating section (S820). When the temperature of the heater 130 is lower than the lower limit of the pre-heating section, the controller 110 starts to raise the temperature of the heater 130 by heating the heater 130 by the first method (S830).

According to the embodiment, operations S810 and S820 may be omitted, and in this case, the controller 110 controls the electric power supplied to the heater 130 by the first method from the time when the heater 130 starts to be heated.

In addition, the controller 110 checks a difference between the current temperature and the upper limit of the pre-heating temperature section, and calculates the time taken to reach the upper limit of the pre-heating temperature section from the current temperature (hereinafter, referred to as "upper limit reaching time") (S840).

The controller 110 checks whether the upper limit reaching time has elapsed (S850), and when the upper limit reaching time has elapsed, the controller 110 changes the control method of the electric power supplied to the heater 130 from the first method to the second method and continuously heats the heater 130 to raise the temperature of the heater 130 to the target temperature (S860). In operation S860, the controller 110 calculates the time taken for the temperature of the heater 130 at the upper limit of the pre-heating temperature section to reach the target temperature (hereinafter, referred to as "target temperature reaching time").

The controller 110 checks whether the target temperature reaching time has elapsed (S870). When the target temperature reaching time has passed, the controller 110 maintains the temperature of the heater 130 at the target temperature by the second method (S880). In operation S880, if the second method is the PID control method, the controller 110 may appropriately adjust the PID gains (proportional term, integral term, and derivative term) to be different before and after the temperature reaches the target temperature.

Figure 9:
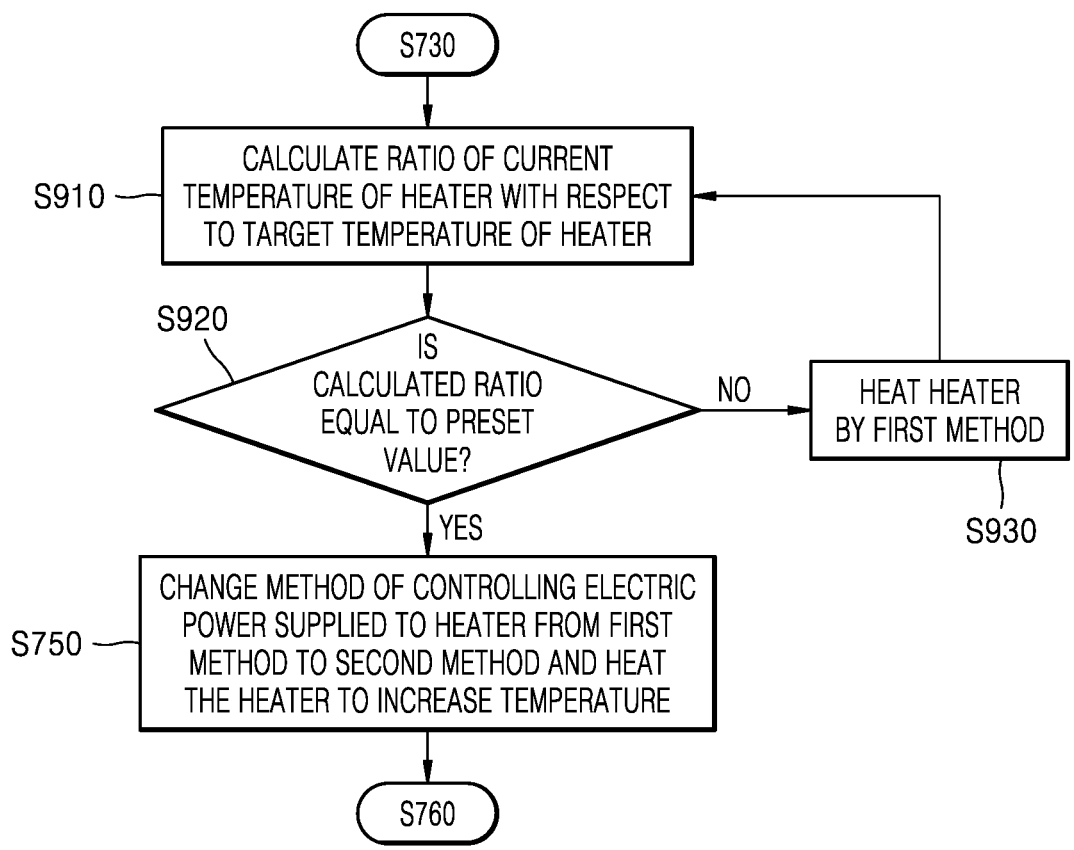
FIG. 9 is a flowchart illustrating an example of a method of controlling electric power supplied to a heater according to another embodiment of the disclosure.

FIG. 9 is a flowchart illustrating an example of a method of controlling electric power supplied to a heater according to another embodiment of the disclosure.

FIG. 9 illustrates a process in which the controller 110 uses the target temperature and the proportional coefficient as in Equation 1 or uses a certain ratio, when determining the upper limit of the pre-heating temperature section for changing the power control method into the second method in FIG. 7.

The controller 110 heats the heater 130 by the first method (S730), and calculates a ratio between the current temperature and the target temperature of the heater 130 (S910).

The controller 110 checks whether the ratio of the current temperature with respect to the target temperature of the heater 130 is equal to a preset value (S920). When the ratio between the current temperature and the target temperature of the heater 130 is equal to the preset value, the controller 110 changes the control method of the electric power supplied to the heater from the first method to the second method and then controls the battery 120 to continuously heat the heater 130 to raise the temperature of the heater (S750). The preset value may be 0.8 or a certain value determined according to Equation 1 in operation S920.

When the ratio between the current temperature and the target temperature of the heater 130 is not equal to the preset value, the controller 110 controls the heater 130 to be heated by the first method so as to sufficiently raise the temperature of the heater 130 (S930).

Figure 10:
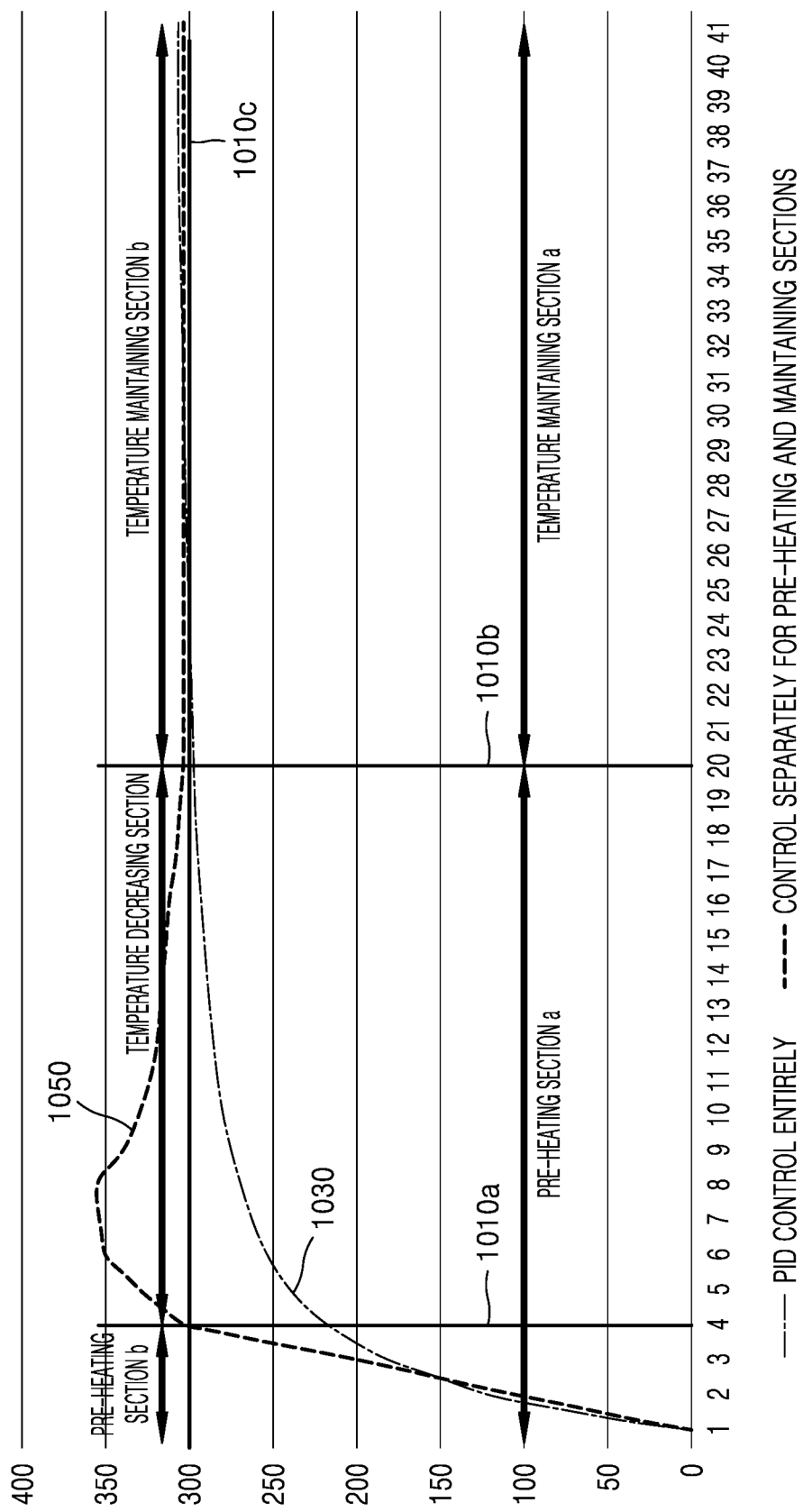
FIG. 10 is a graph illustrating a method of controlling a temperature of a heater in an aerosol generator according to sections.

FIG. 10 is a graph illustrating a method of controlling a temperature of a heater in an aerosol generator according to sections.

Referring to FIG. 10, the graph of FIG. 10 includes boundary lines 1010a, 1010b, and 1010c for illustrating sections that are partitioned according to the temperature of the heater, a temperature variation curve 1030 of the heater according to the related art, and a temperature variation curve 1050 of the heater according to an embodiment. In FIG. 10, a transverse axis denotes time in seconds and a longitudinal axis denotes Celsius temperature.

According to the related art, the controller tends to use the PID control in order to prevent the temperature of the heater from rising excessively during the pre-heating. When the controller controls the temperature of the heater in the PID control method, the temperature of the heater slowly rises through a feedback algorithm peculiar to the PID, and the heater reaches the target temperature, e.g., 300° C., after passing through a pre-heating section a that is set from 0 to 20 sec. When the temperature of the heater reaches 300° C., the controller enters a maintaining section a for maintaining the temperature of the heater at 300° C. However, according to the related art, the power control method of the controller is not changed at a boundary between the pre-heating section a and the temperature maintaining section a, but the temperature of the heater is controlled by adjusting gains of the proportional term, the integral term, and the derivative term according to the characteristics of the PID control.

According to the temperature variation curve 1030 of the heater according to the related art, the temperature of the heater steadily increases in the pre-heating section a as described above, and reaches the target temperature, that is, 300° C., at 20 sec. and enters the temperature maintaining section a. The time taken for the heater to reach the target temperature (20 sec.) may vary depending on a material of the heater, an output voltage of the battery, etc., and the target temperature (300° C.) of the heater may also vary depending on the aerosol generating material.

On the other hand, according to the temperature variation curve 1050 according to the disclosure, the temperature of the heater rapidly increases in a pre-heating section b and reaches the target temperature, e.g., 300° C., at 4 sec., and then enters a temperature decreasing section. According to the disclosure, the controller 110 may use the PWM control method having a fixed output level in the pre-heating section b, without using the PID control method.

Here, the temperature decreasing section is not shown in the temperature variation curve 1030 of the heater according to the related art. The temperature decreasing section refers to a time period in which controller 110 controls the electric power supplied to the heater in order to decrease the temperature of the heater to the target temperature when the overshoot occurs by the heater temperature reaching the target temperature rapidly and exceeding the target temperature. According to the related art, there is no temperature decreasing section because there is no overshoot occurring in the heater, but according to the embodiment, the power controlling process of the controller 110 for rapidly removing the overshoot of the heater is included.

Then, when the temperature of the heater returns to the target temperature after the temperature decreasing section, the controller 110 enters a temperature maintaining section b in order to maintain the temperature of the heater constant. As described above, according to the embodiment of the disclosure, the pre-heating time may be greatly reduced and a sufficient amount of aerosol provided to the user may be ensured at an early stage.

Hereinafter, processes of operating the aerosol generator which controls the temperature of the heater for each section according to the exemplary embodiment will be described in detail with reference to FIGS. 5 and 10. The pre-heating section, the temperature decreasing section, and the temperature maintaining section may be respectively referred to as a first stage, a second stage, and a third stage, or may be respectively referred to as a first section, a second section, and a third section, given that controlling methods or section characteristics of respective sections are different from one another.

The controller 110 controls the temperature of the heater 130 differently in the pre-heating section, the temperature decreasing section, and the temperature maintaining section.

Here, the pre-heating section denotes a time period in which the temperature of the heater is lower than the target temperature. The pre-heating section may be a section for re-heating the heater when the temperature of the heater is lower than the target temperature because the user maintains the aerosol generator 100 in turned-off status or the electric power is not supplied to the heater since a predetermined time has passed after the aerosol generator 100 is turned on by the user.

The controller 110 may allow the electric power to be rapidly supplied to the heater by using a maximum output according to a status of the battery in the pre-heating section. Here, the status of the battery may collectively refer to factors that directly affect the amount of electric power supplied by the battery to the heater, e.g., an output voltage level of the battery, a charged amount of the battery, etc. The controller 110 may control the temperature of the heater to be rapidly increased in the fixed PWM control method when controlling the electric power of the battery to be supplied to the heater in the pre-heating section. In addition, in FIG. 6, the pre-heating section b of the aerosol generator 100 according to the disclosure is 4 sec., but the pre-heating section b may be increased or reduced according to the elements included in the aerosol generator 100.

In addition, when the temperature of the heater reaches the target temperature, the controller 110 may change the method of controlling the electric power supplied to the heater from the method corresponding to the pre-heating section to the method corresponding to the temperature decreasing section. Here, the method corresponding to the pre-heating section and the method corresponding to the temperature decreasing section may be stored in the storage device 170 in the form of a temperature profile of the heater, and then may be delivered to the controller 110 according to the call of the controller 110. The temperature decreasing section denotes a time period in which the controller 110 controls the heater to decrease the temperature of the heater when the overshoot occurs by the temperature of the heater exceeding the target temperature. The temperature to which the temperature of the heater having the overshoot has to decrease becomes the target temperature, which is 300° C. in the example of FIG. 10.

In the above processes, the controller 110 performs the PID control for decreasing the temperature of the heater to the target temperature after receiving the temperature profile and the PID control instructions stored in the storage device 170, and in particular, the controller 110 may adjust the gain of the derivative term appropriately in order to decrease the temperature of the heater which already has exceeded the target temperature. The gains of the proportional term, the integral term, and the derivative term stored in the storage device 170 may be obtained in advance through experiments. Also, a gain calculation module (not shown) for the PID control may be included in the storage device 170 for calculating an appropriate gain at a certain temperature of the heater at a certain time point.

The controller 110 may include a temperature sensor that regularly or irregularly measures the temperature of the heater in order to distinguish the pre-heating section from the temperature decreasing section. Also, the controller 110 may include a timer for measuring lengths of the pre-heating section and the temperature decreasing section. The temperature of the heater and the lengths of the pre-heating section and the temperature decreasing section collected by the controller 110 may be stored in the storage device 170, read by the call of the controller 110, and used to calculate a controlling parameter by the controller 110.

Lastly, the controller 110 controls the temperature of the heater to be maintained at the target temperature when the temperature of the heater, in which the overshoot has occurred, is decreased to the target temperature during the temperature decreasing section. The time period in which the controller 110 maintains the temperature of the heater at the target temperature may be defined as the temperature maintaining section. The controller 110 controls the electric power supplied to the heater by using the PID control method while the temperature of the heater is maintained at the target temperature, and when a preset time has passed, the controller 110 recognizes that the temperature maintaining section is ended and controls the electric power to the heater to be blocked.

The controller 110 calculates the control reference ratio by using at least two of the lengths of the pre-heating section, the temperature decreasing section, and the temperature maintaining section, and may control the electric power supplied to the heater based on the control reference ratio.

$$K_1 = \frac{t_1}{t_2} \qquad \text{[Equation 2]}$$

Equation 2 shows an example of the control reference ratio that may be calculated by the controller 110. In Equation 2, k1 denotes the control reference ration, t1 denotes the length of the pre-heating section, and t2 denotes the length of the temperature decreasing section. The controller 110 may calculate the control reference ratio according to Equation 2, and may appropriately adjust the length of the temperature decreasing section based on the calculated control reference ratio.

$$K_1 < C_1 \qquad \text{[Equation 3]}$$

Equation 3 shows an example in which the controller 110 compares the control reference ratio with a preset comparison control value. In Equation 3, k1 denotes the control reference ratio calculated according to Equation 2, and C1 denotes a comparison control value set in advance to be compared with the control reference ratio. The comparison control value may be stored in the storage device 170 and may be delivered to the controller 110 according to a request from the controller 110. The comparison control value may be updated if necessary.

As an example, the comparison control value may have a value of 2. In this case, the length of the temperature decreasing section has to be greater than half the length of the pre-heating section, considering Equations 2 and 3. Once the length of the pre-heating section is determined via the timer and the temperature sensor, the controller 110 may calculate how long the temperature decreasing section has to be maintained based on the length of the pre-heating section which is a constant. In detail, the controller 110 may determine the gains of the proportional term, the integral term, and the derivative term for performing the PID control, taking into account how many seconds at least has to be maintained for the temperature decreasing section.

When the temperature of the heater enters the temperature maintaining section after the pre-heating section and the temperature decreasing section, the controller 110 re-calculates and updates the control reference ratio based on the determined lengths of the pre-heating section and the temperature decreasing section, and may maintains the temperature maintaining section according to the updated control reference ratio.

$$K_2 = \frac{t_2}{t_3} \qquad \text{[Equation 4]}$$

Equation 4 shows another example of the control reference ratio that may be calculated by the controller 110. In detail, in Equation 4, k2 denotes an updated control reference ratio (hereinafter, referred to "updated control reference ratio") that is updated from k1. Also, t2 denotes a length of the temperature decreasing section, and t3 denotes a length of the temperature maintaining section. The controller 110 may calculate the control reference ratio according to Equation 4, and may appropriately adjust the length of the temperature maintaining section based on the calculated control reference ratio.

$$K_2 = \frac{t_1 + t_2}{t_3} \qquad \text{[Equation 5]}$$

Equation 5 shows another example of the updated control reference ratio that may be calculated by the controller 110. In Equation 5, k2 denotes the updated control reference ratio, and t1 to t3 respectively denote lengths of the pre-heating section, the temperature decreasing section, and the temperature maintaining section. The controller 110 may calculate and update the control reference ratio according to Equation 4 or 5, and may appropriately adjust the length of the temperature maintaining section based on the updated control reference ratio.

$$K_2 < C_2 \qquad \text{[Equation 6]}$$

Equation 6 shows an example in which the controller 110 compares the updated control reference ratio with a preset comparison control value. In Equation 6, k2 denotes the updated control reference ratio calculated according to Equation 4 or 5 above, and C2 denotes a comparison control value set in advance for comparison with the updated control reference ratio. The comparison control value may be stored in the storage device 170 and may be delivered to the controller 110 according to a request from the controller 110. Also, the comparison control value may be updated if necessary.

As an example, the comparison control value may have a value of 1. In this case, the length of the temperature maintaining section has to be greater than the length of the temperature decreasing section, considering Equation 4 and Equation 6. Also, when the updated control reference ratio is calculated according to Equation 4, the comparison control value of 1 requires that the length of the temperature maintaining section be greater than the sum of the lengths of the pre-heating section and the temperature decreasing section. The controller 110 may selectively calculate the updated control reference ratio according to Equation 4 or Equation 5 above, in order to appropriately adjust the gain of the PID.

As described above, the length of the temperature maintaining section is restricted according to the lengths of the pre-heating section and the temperature decreasing section, and thus, carbonizing of the medium, which occurs when the temperature of the heater is maintained at the high temperature, may be reduced. According to the embodiment, a sufficient amount of aerosol may be rapidly provided to the user with a short period of pre-heating time, and moreover, the carbonizing of the medium may be reduced. As a result, the user may have a satisfactory aerosol smoking experience.

In an embodiment, the controller may determine lengths of the temperature decreasing section and the temperature maintaining section according to Equations 2, 3, 4, and 6, and may control the temperature of the heater for each section. In an alternative embodiment, the controller may determine lengths of the temperature decreasing section and the temperature maintaining section according to Equations 2, 3, 5, and 6, and may control the temperature of the heater for each section. As described above, the lengths of the temperature decreasing section and the temperature maintaining section are dependent upon the length of the pre-heating section that may vary depending on the material of the heater and an initial temperature of the heater.

Figure 11:
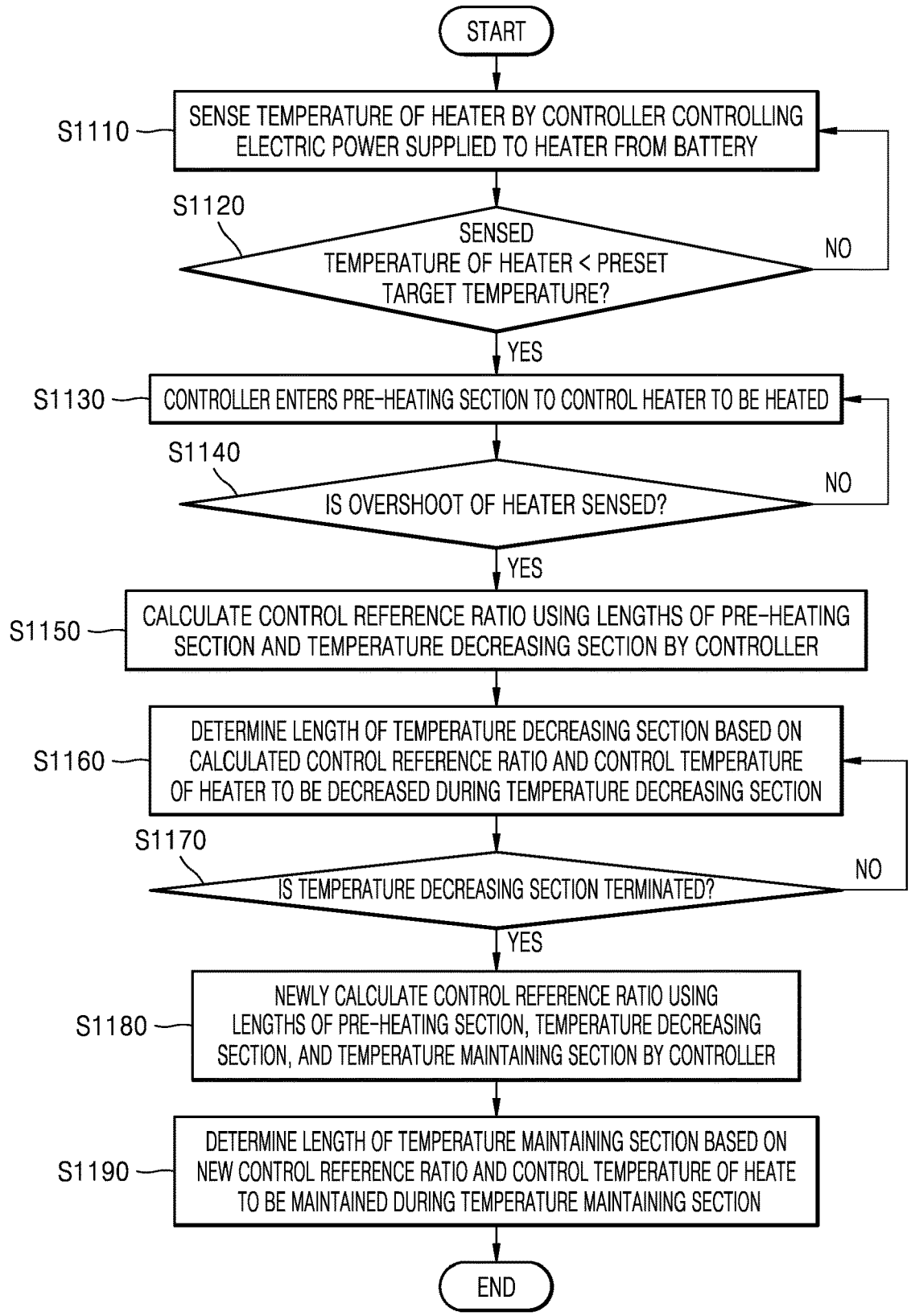
FIG. 11 is a flowchart illustrating an example of a method of controlling a temperature of a heater in an aerosol generator according to sections, according to an embodiment of the disclosure.

FIG. 11 is a flowchart illustrating an example of a method of controlling a temperature of a heater in an aerosol generator according to sections, according to an embodiment of the disclosure.

Since the method illustrated with reference to FIG. 11 may be implemented by the aerosol generator 10 of FIG. 5, descriptions below will be provided with reference to FIG. 5 and descriptions that are already described above with reference to FIGS. 5 and 10 are omitted.

The controller senses the temperature of the heater (S1110), and checks whether the sensed temperature of the heater is lower than a target temperature set in advance (S1120).

When the temperature of the heater is lower than the target temperature, the controller enters the pre-heating section to control the heater to be heated (S1130).

The controller checks whether an overshoot of the heater is sensed while regularly or irregularly monitoring rising of the temperature of the heater through the temperature sensor (S1140), and when the overshoot is sensed, the controller calculates the control reference ratio by using the lengths of the pre-heating section and the temperature decreasing section (S1150).

The controller determines the length of the temperature decreasing section based on the calculated control reference ratio, and controls the heater to decrease the temperature during the temperature decreasing section (S1160).

In an embodiment, the controller may control the electric power supplied to the heater based on a result of comparing the control reference ratio with the preset comparison control value as described above with reference to FIG. 10.

The controller checks whether the temperature decreasing section is terminated based on the temperature of the heater or the lapse of time (S1170). When the temperature decreasing section is terminated, the controller calculates the control reference ratio based on at least two of the pre-heating section, the temperature decreasing section, and the temperature maintaining section (S1180). In operation S1180, the controller may use at least one of the temperature sensor or the timer in order to check the termination of the temperature decreasing section.

The controller updates the control reference ratio calculated in operation S1150 with the control reference ratio calculated in operation S1180, determines the length of the temperature maintaining section based on the updated control reference ratio, and then, controls the temperature of the heater to be maintained at the target temperature during the temperature maintaining section (S1190).

Figure 12:
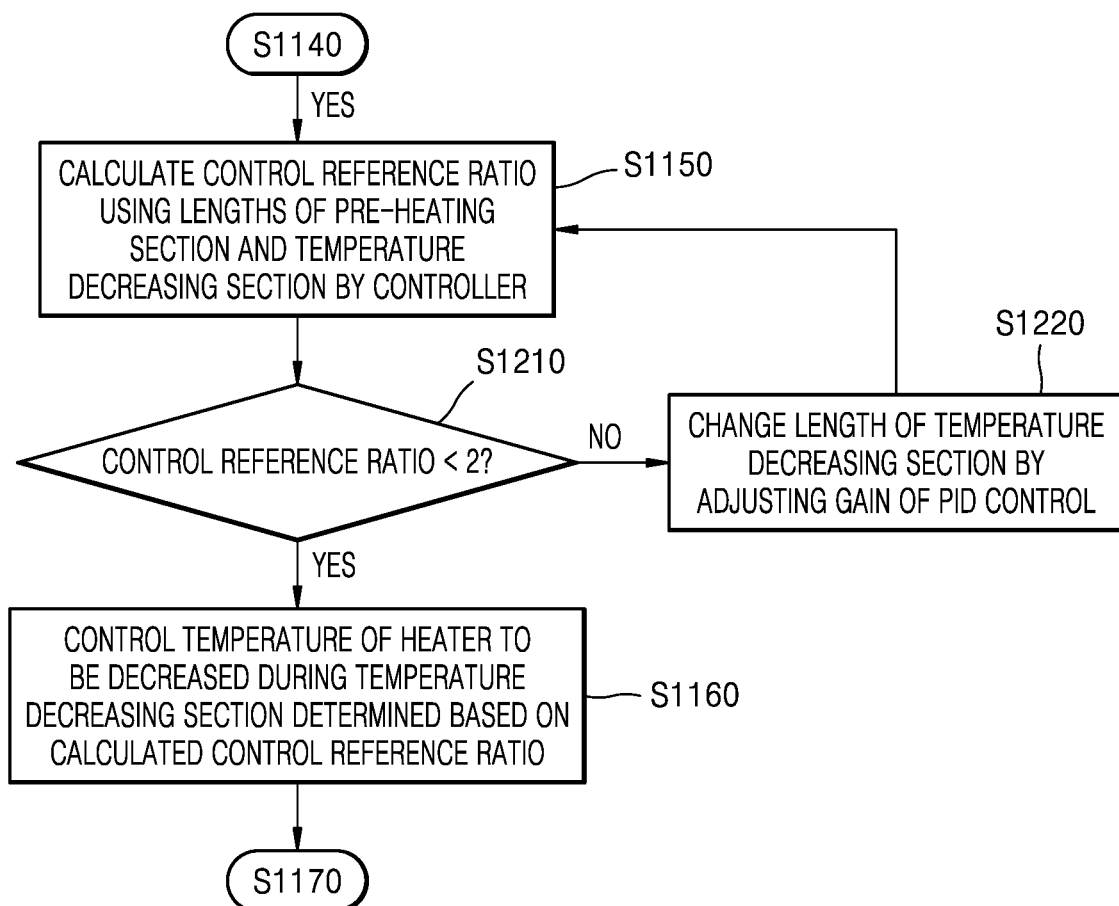
FIG. 12 is a flowchart illustrating an example in which a controller determines a period of a temperature reduction section.

FIG. 12 is a flowchart illustrating an example, in which a controller determines a period of a temperature reduction section.

FIG. 12 illustrates an alternative embodiment of operations S1140 to S1170 shown in FIG. 11, and hereinafter, descriptions will be provided with reference to FIG. 11 for convenience of description.

When the controller senses the overshoot of the heater (S1140), the controller calculates the control reference ratio by using the lengths of the pre-heating section and the temperature decreasing section (S1150).

The controller compares the control reference ratio calculated in operation S1150 with the comparison control value, e.g., 2 (S1210).

When the control reference ratio is equal to or greater than 2 in operation S1210, the controller changes the length of the temperature decreasing section by adjusting the gain of the PID control method (S1220). The control reference ratio may be re-calculated through operation S1150, due to operation S1220.

When the control reference ratio is less than 2 in operation S1210, the controller controls the temperature of the heater to be decreased during the temperature decreasing section determined based on the calculated control reference ratio (S1160).

Figure 13:
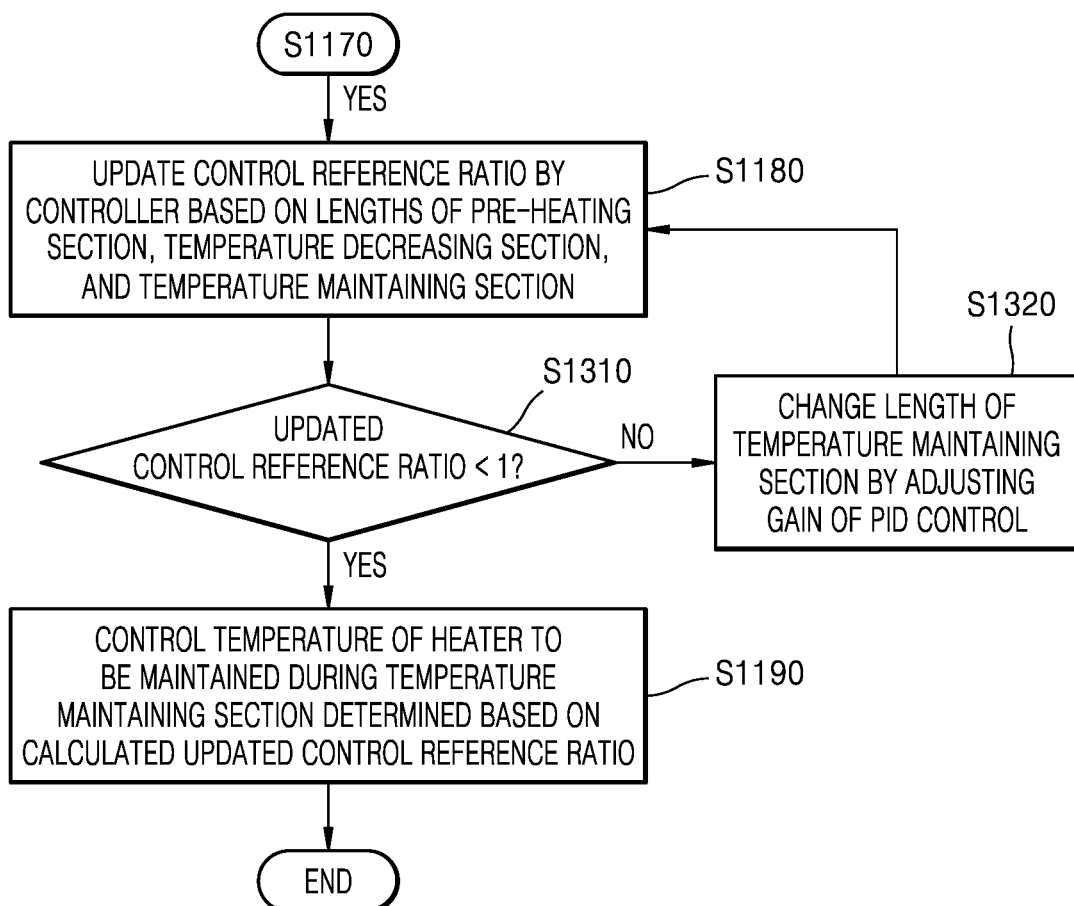
FIG. 13 is a flowchart illustrating an example in which a controller determines a period of a temperature maintaining section.

FIG. 13 is a flowchart illustrating an example, in which a controller determines a period of a temperature maintaining section.

FIG. 13 illustrates an alternative embodiment of operations S1170 to S1190 shown in FIG. 11, and hereinafter, descriptions will be provided with reference to FIG. 11 for convenience of description.

When the controller senses that the temperature decreasing section is terminated (S1170), the controller calculates the updated control reference ratio based on at least two of the lengths of the pre-heating section, the temperature decreasing section, and the temperature maintaining section (S1180).

The controller determines whether the updated control reference ratio calculated in operation S1180 is less than 1 (S1310).

When the updated control reference ratio is equal to or less than 1, the controller changes the length of the temperature maintaining section by adjusting the gain of the PID control (S1320). The updated control reference ratio may be re-calculated through operation S1180, due to operation S1320.

When the updated control reference ratio is less than 1, the controller controls the temperature of the heater to be maintained at the target temperature during the temperature maintaining section determined based on the updated control reference ratio calculated by the controller (S1390).

Figure 14:
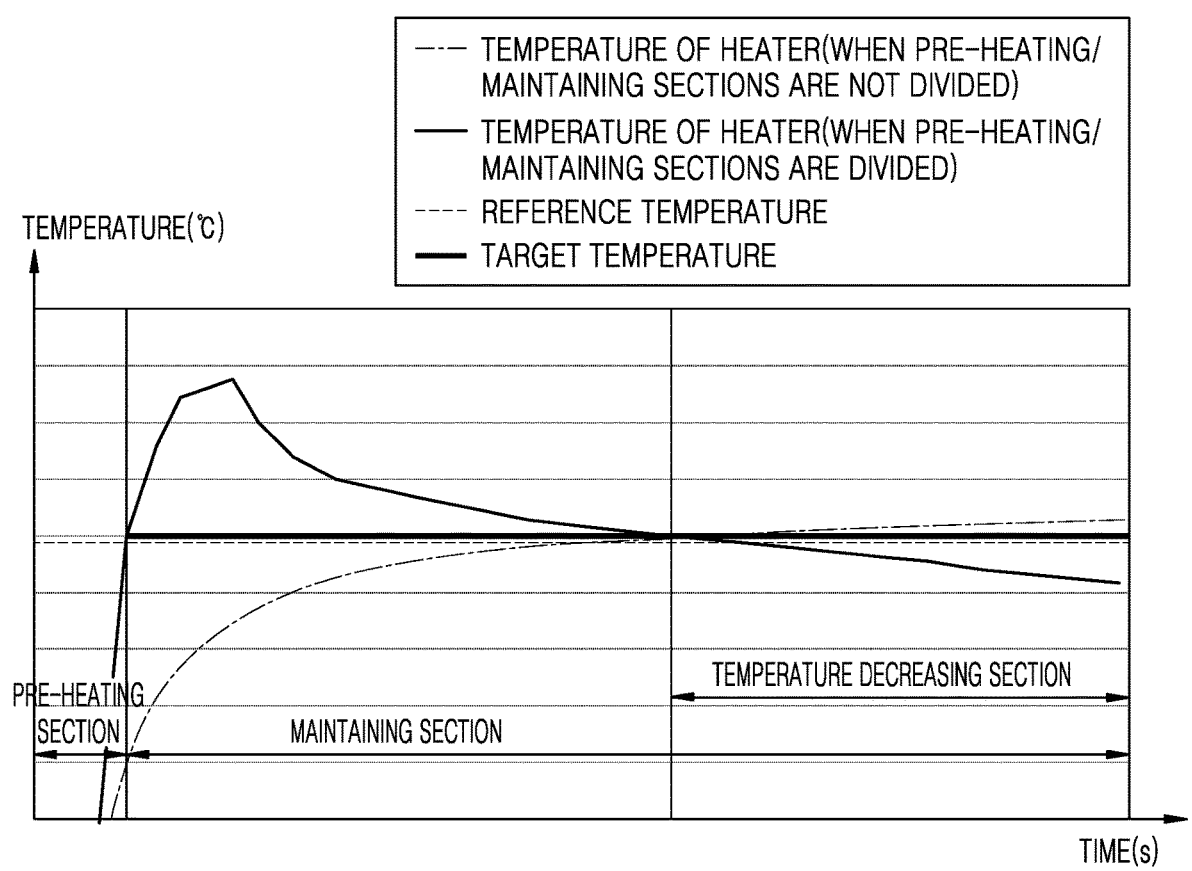
FIG. 14 is a graph for describing differences of the method of controlling the temperature of the heater separately for the pre-heating section and the maintaining section from the method of controlling the temperature without dividing the sections according to the related art, and issues of the method of controlling the temperature for each section.

FIG. 14 is a graph for describing differences between the method of controlling the temperature of the heater differently in the pre-heating section and the maintaining section and the method of controlling the temperature without dividing the sections according to the related art, and issues of the method of controlling the temperature for each section.

Referring to FIG. 14, the graph shows the variation in the temperature of the heater 130 according to the method of controlling the temperature of the heater 130 differently in the pre-heating section and the maintaining section, and the variation in the temperature of the heater 130 according to the method of controlling the temperature of the heater 130 for the entire section without distinction between the pre-heating section and the maintaining section. Also, when the temperature of the heater is controlled differently in the pre-heating section and the maintaining section, the target temperature of the heater 130 is set as a constant value.

The controller 110 may control the temperature of the heater 130 to be maintained at a reference temperature. The reference temperature may denote a temperature that is suitable for generating aerosol from the cigarette 200. The reference temperature may set differently according to the kind of the cigarette 200. For example, the reference temperature may be set between 240° C. and 360° C.

The controller 110 may set the target temperature and control the temperature of the heater 130 to reach the target temperature. The target temperature may be set to be the same as the reference temperature. However, one or more embodiments are not limited thereto, that is, the target temperature may be different from the reference temperature for appropriately controlling the temperature of the heater 130.

In the case of the method of controlling the temperature of the heater 130 differently in the pre-heating section and the maintaining section, the controller 110 may control the electric power supplied to the heater 130 so that the temperature of the heater 130 is equal to or greater than the reference temperature in the pre-heating section. The pre-heating section may refer to a time period in which the heater 130 is heated to be equal to or greater than the reference temperature. Referring to the example shown in FIG. 14, the reference temperature is set to be 300° C. and the section before the temperature of the heater 130 is greater than the reference temperature corresponds to the pre-heating section.

In the pre-heating section, the controller 110 may control the electric power supplied to the heater 130 so that the temperature of the heater 130 is equal to or greater than the reference temperature within a short period of time. For example, the controller 110 may set a frequency and a duty cycle of a current pulse supplied from the battery 120 to the heater 130 through a pulse-width modulation to the maximum values.

In the case of the method of controlling the temperature of the heater 130 differently in the pre-heating section and the maintaining section, the controller 110 may set the target temperature of the heater 130 and control the electric power supplied to the heater 130 so that the temperature of the heater 130 is maintained at the reference temperature in the maintaining section. The maintaining section may denote a section after the pre-heating section is terminated when the temperature of the heater 130 is equal to or greater than the reference temperature. Referring to the example of FIG. 14, the section after the point when the temperature of the heater 130 is greater than the reference temperature, e.g., 300° C., may correspond to the maintaining section.

In the maintaining section, the controller 110 may set the target temperature. In particular, the controller 110 may set the target temperature at the point when the pre-heating section is terminated and the maintaining section starts. Referring to the example of FIG. 14, the target temperature is set at the point when the pre-heating section is terminated and the maintaining section starts, and is maintained constant thereafter. Also, the target temperature is set to be equal to the reference temperature, e.g., 300° C.

In the maintaining section, the controller 110 may control the electric power supplied to the heater 130 to decrease the temperature of the heater 130, which has increased greater than the reference temperature within a short period of time, to the reference temperature of the heater 130. In particular, coefficients of the PID control method may be set by the controller 110 such that the temperature of the heater 130 may be reduced to and maintained at the reference temperature. Referring to the example of FIG. 14, the temperature of the heater 130 which has increased to higher than the reference temperature through the pre-heating section is reduced in the maintaining section.

In the maintaining section, by the PID coefficients set to reduce the temperature of the heater 130, the temperature of the heater 130 may decrease to be equal to or lower than the reference temperature. Since the heater 130 is heated to be equal to or higher than the reference temperature within the short period of time in the pre-heating section, the time for the temperature of the heater 130 to reach the reference temperature or higher may be reduced. However, it may be difficult to maintain the temperature of the heater 130 at the reference temperature in the maintaining section.

Referring to the example of FIG. 14, as the smoking is executed, the temperature of the heater 130 is gradually decreased below the reference temperature. Since the cigarette 200 may sufficiently generate the aerosol at the reference temperature, the temperature of the heater 130 decreasing below the reference temperature may cause degradation of smoking quality.

The controller 110 may adjust the target temperature in order to compensate for the temperature of the heater 130, which is decreased below the reference temperature. The compensation of the temperature of the heater 130 may be performed in the manner that the temperature of the heater 130 is increased by the extent that the temperature of the heater 130 decreases below the reference temperature.

In order to address the issue that the temperature of the heater 130 is decreased below the reference temperature, which occurs when the target temperature is maintained constant without being adjusted, the controller 110 may adjust the target temperature in various manners. Accordingly, the controller 110 may compensate for the temperature of the heater 130, which decreases below the reference temperature, so as to maintain the temperature of the heater 130 close to the reference temperature.

The controller 110 may adjust the target temperature in the temperature decreasing section, in which the temperature of the heater 130 decreases below the reference temperature. The controller 110 may adjust the target temperature at the time point when the temperature of the heater 130 decreases below the reference temperature and the temperature decreasing section starts. Alternatively, the controller 110 may adjust the target temperature before or after the temperature decreasing section starts.

The controller 110 may adjust the target temperature in real-time. The controller 110 may determine the target temperature in real-time based on the temperature variation of the heater 130, etc. However, one or more embodiments are not limited thereto, that is, the controller 110 may change the target temperature to another value only once.

Since the controller 110 compensates for the temperature of the heater 130 by adjusting the target temperature, the temperature of the heater 130 may be maintained around the reference temperature, and accordingly, degradation in the smoking quality due to the decrease in the temperature may be prevented. Therefore, since the pre-heating section and the maintaining section are divided, the time taken to prepare the aerosol generator 10 for providing the user with the aerosol may be reduced, and at the same time, since the heater 130 is heated within a short period of time in the pre-heating section, the reduction in the temperature of the heater 130 in the maintaining section may be prevented.

Referring to FIG. 14, the method of controlling the temperature of the heater 130 throughout the entire section without dividing the pre-heating section and the maintaining section is shown. When the pre-heating section and the maintaining section are not divided, the temperature dropping as the smoking proceeds may not occur, but the time taken for the temperature of the heater 130 to reach the reference temperature increases longer than that in a case in which the pre-heating section and the maintaining section are divided, and accordingly, the time for preparing the aerosol generator 10 may increase. Referring to the example of FIG. 14, when the pre-heating section and the maintaining section are not divided, it takes more time for the temperature of the heater 130 to reach the reference temperature than the case in which the pre-heating section and the maintaining section are divided.

Figure 15:
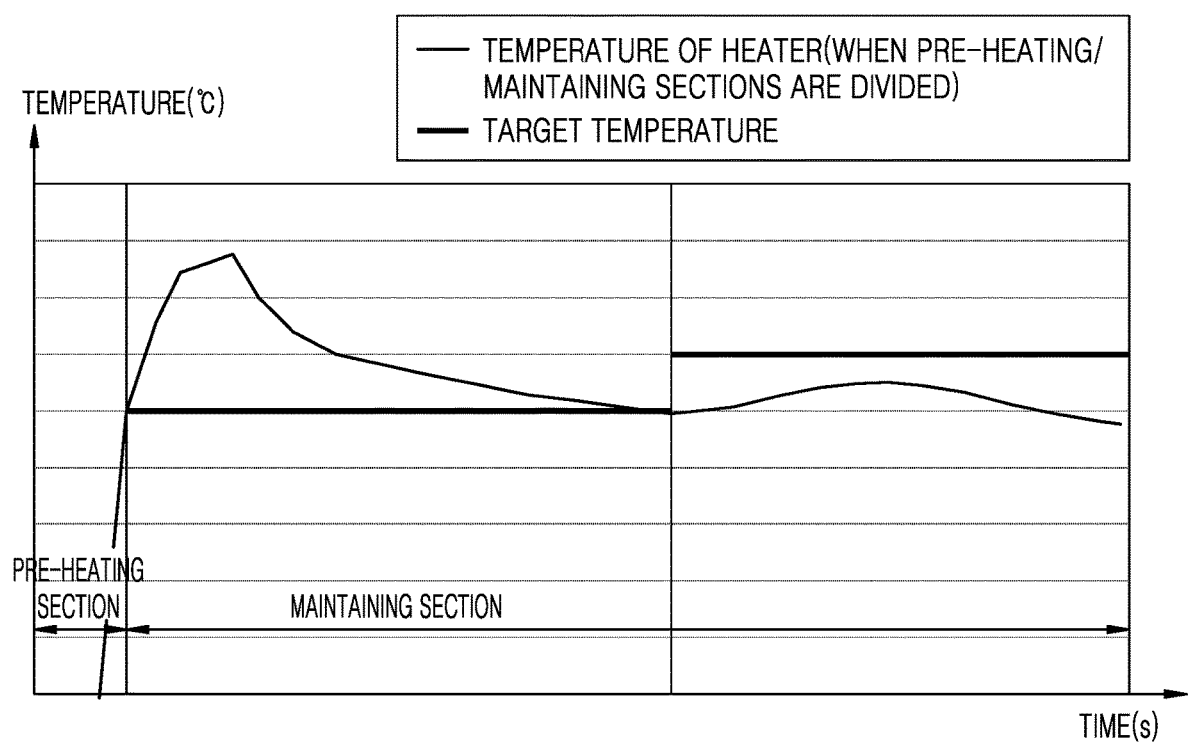
FIG. 15 is a graph illustrating an example of adjusting a target temperature according to one or more embodiments of the disclosure.

FIG. 15 is a graph illustrating an example of adjusting a target temperature according to one or more embodiments of the disclosure.

The controller 110 may adjust the target temperature by changing the target temperature once. Referring to the example of FIG. 15, the target temperature is changed to a greater constant value when the temperature decreasing section starts, and the temperature of the heater 130 is controlled accordingly.

When the target temperature is adjusted by changing the target temperature once, the temperature of the heater 130 may be maintained closer to the reference temperature as compared with a case in which the target temperature is not adjusted. Also, due to a simple process of adjusting the target temperature, power consumption may be reduced and a circuit structure of the controller 110 may be simplified.

Figure 16:
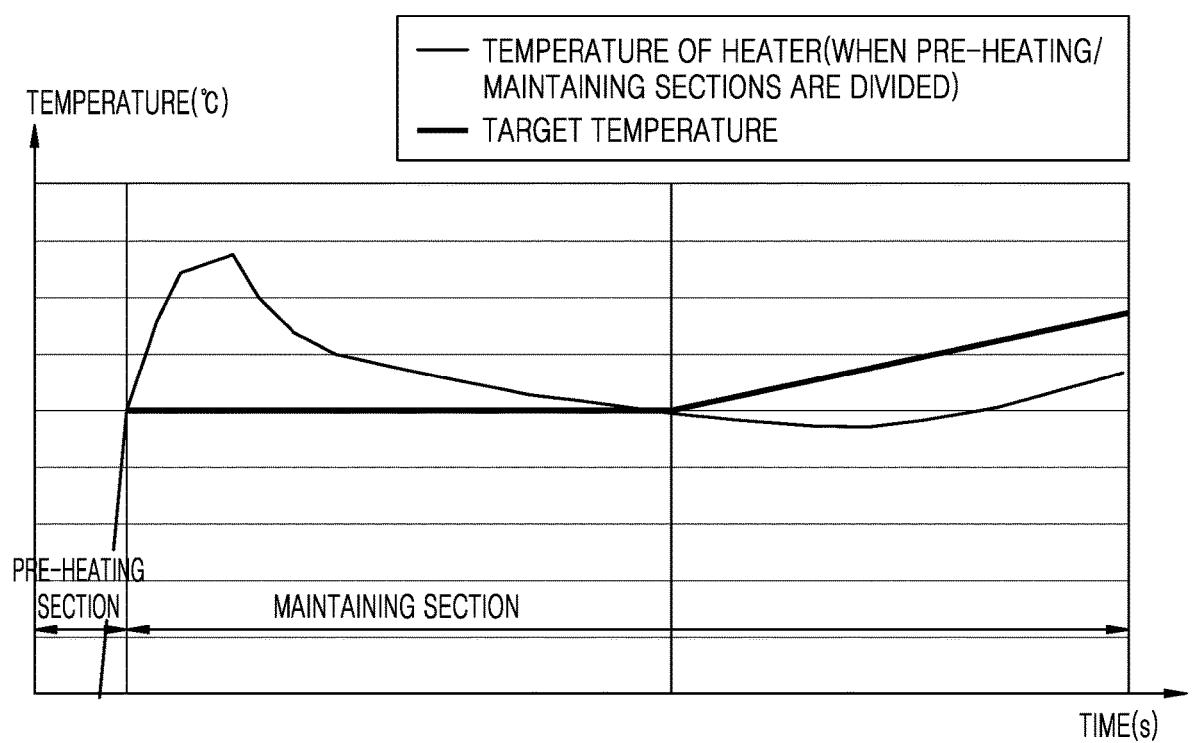
FIG. 16 is a graph illustrating another example of adjusting a target temperature according to one or more embodiments of the disclosure.

FIG. 16 is a graph illustrating another example of adjusting a target temperature according to one or more embodiments of the disclosure.

The controller 110 may adjust the target temperature by changing the target temperature linearly. Referring to the example of FIG. 16, the target temperature is increased linearly from the time point when the temperature decreasing section starts, and the temperature of the heater 130 is controlled accordingly.

When the target temperature is adjusted by changing the target temperature linearly, the temperature of the heater 130 may be maintained closer to the reference temperature as compared with a case in which the target temperature is not adjusted. Also, since it is not complicated for the controller 110 to adjust the target temperature in this way, the power consumption may be reduced and circuit design may be easy.

The target temperature may be simply adjusted in the method illustrated in FIGS. 15 and 16 to compensate for the temperature of the heater 130, but when the smoking is performed for a long time period, there may be a difference between the temperature of the heater 130 and the reference temperature. Thus, a method of more precisely adjusting the target temperature may be suggested. In the process of designing the control method and the aerosol generator 10 according to the disclosure, values shown as examples in FIG. 17 may be utilized to adjust the target temperature.

Figure 17:
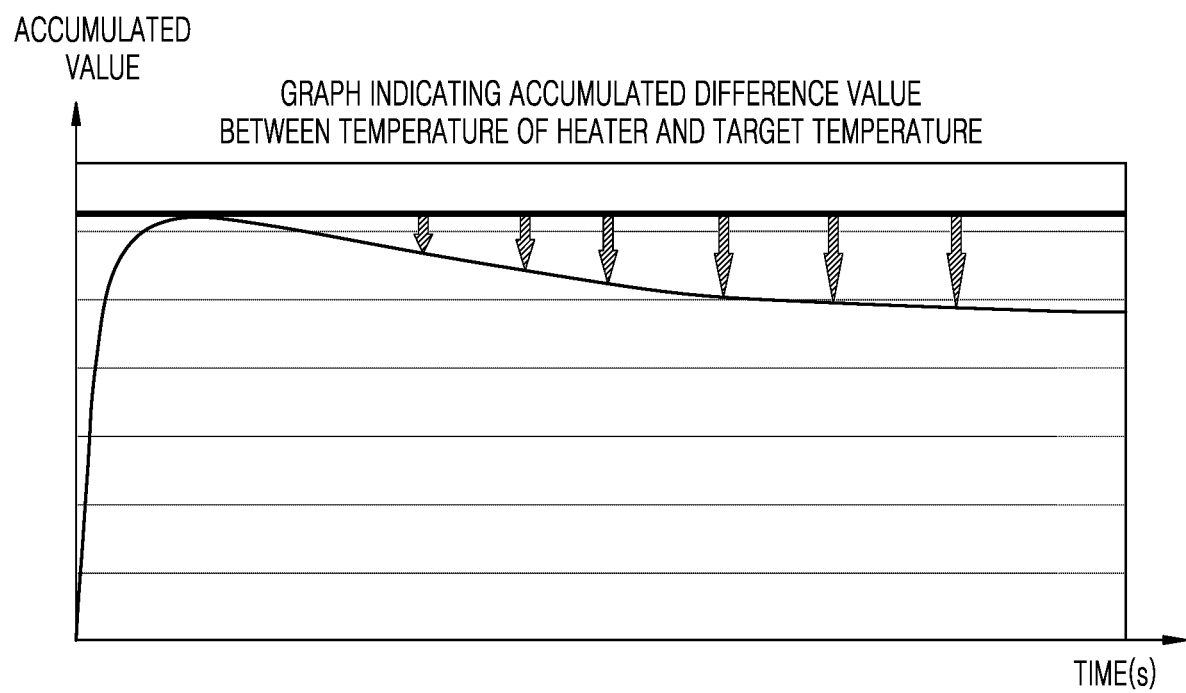
FIG. 17 is a graph illustrating an accumulated value obtained by accumulating a difference value between a temperature of a heater and a target temperature according to time, according to one or more embodiments of the disclosure.

FIG. 17 is a graph illustrating an accumulated value obtained by accumulating a difference value between a temperature of a heater and a target temperature according to time, according to one or more embodiments of the disclosure.

Referring to FIG. 17, an accumulated value obtained by accumulating differences between the temperature of the heater 130 and the target temperature with the lapse of time is shown. In a section in which the temperature of the heater 130 is greater than the target temperature, the difference value has a positive value and the accumulated value may increase. In a section in which the temperature of the heater 130 is lower than the target temperature, the difference value has a negative value and the accumulated value may decrease. Therefore, the accumulated value of FIG. 17 may be the maximum at the point when the temperature of the heater 130 decreases below the target temperature.

The controller 110 may adjust the target temperature based on the accumulated value that is obtained by accumulating the difference value between the temperature of the heater 130 and the target temperature with the lapse of time. The controller 110 may calculate the difference value between the temperature of the heater 130, which is measured in real-time, and the target temperature. Also, the controller 110 may calculate the accumulated value by accumulating the difference value, and adjust the target temperature based on the accumulated value. Therefore, the difference value, the accumulated value, and the target temperature affect one another, and may be calculated and changed in real-time by the controller 110.

For example, the controller 110 may calculate a reduction degree of the accumulated value from the maximum value of the accumulated value, and may adjust the target temperature by adding the decreased value that is obtained by multiplying the reduction degree by a constant to the initial value. The initial value may be the same as the target temperature set by the controller 110 in the maintaining section. The target temperature may be adjusted so that the section in which the accumulated value decreases in FIG. 17 may increase in an inverted form. The detailed method of adjusting the target temperature and the temperature of the heater 130 which is compensated for according to the adjusting of the target temperature are shown in FIG. 6.

Figure 18:
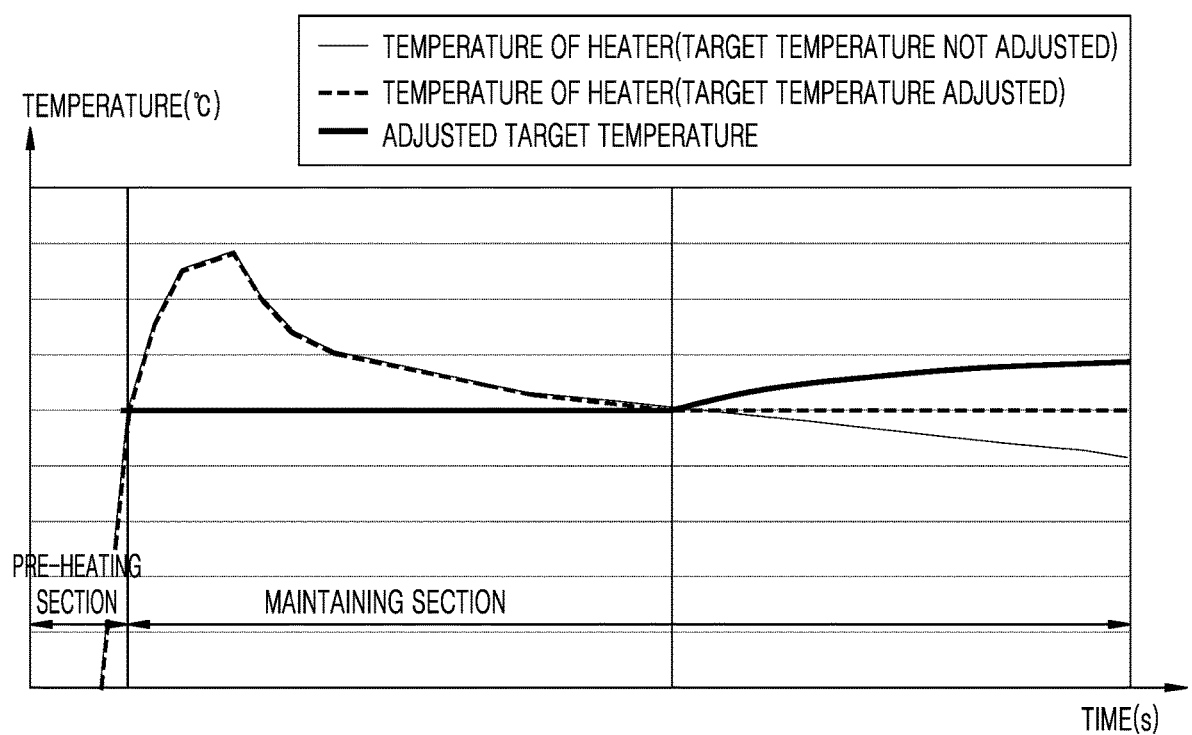
FIG. 18 is a graph illustrating an example of adjusting a target temperature based on a variation in an accumulated value, according to one or more embodiments of the disclosure.

FIG. 18 is a graph illustrating an example of adjusting a target temperature based on a variation in an accumulated value, according to one or more embodiments of the disclosure.

The controller 110 may continuously adjust the target temperature based on the variation in the accumulated value. FIG. 18 shows the variation in the temperature of the heater 130 when the target temperature is adjusted based on the variation in the accumulated value and the variation in the temperature of the heater 130 when the target temperature is not changed but maintained constant.

As the controller 110 adjusts the target temperature based on the variation in the accumulated value, the temperature of the heater 130 may be maintained close to the reference temperature even when the user smokes the aerosol. Therefore, the aerosol generator 10 may generate the aerosol evenly from the cigarette 200 without degradation in the smoking quality even when the time passes.

Figure 19:
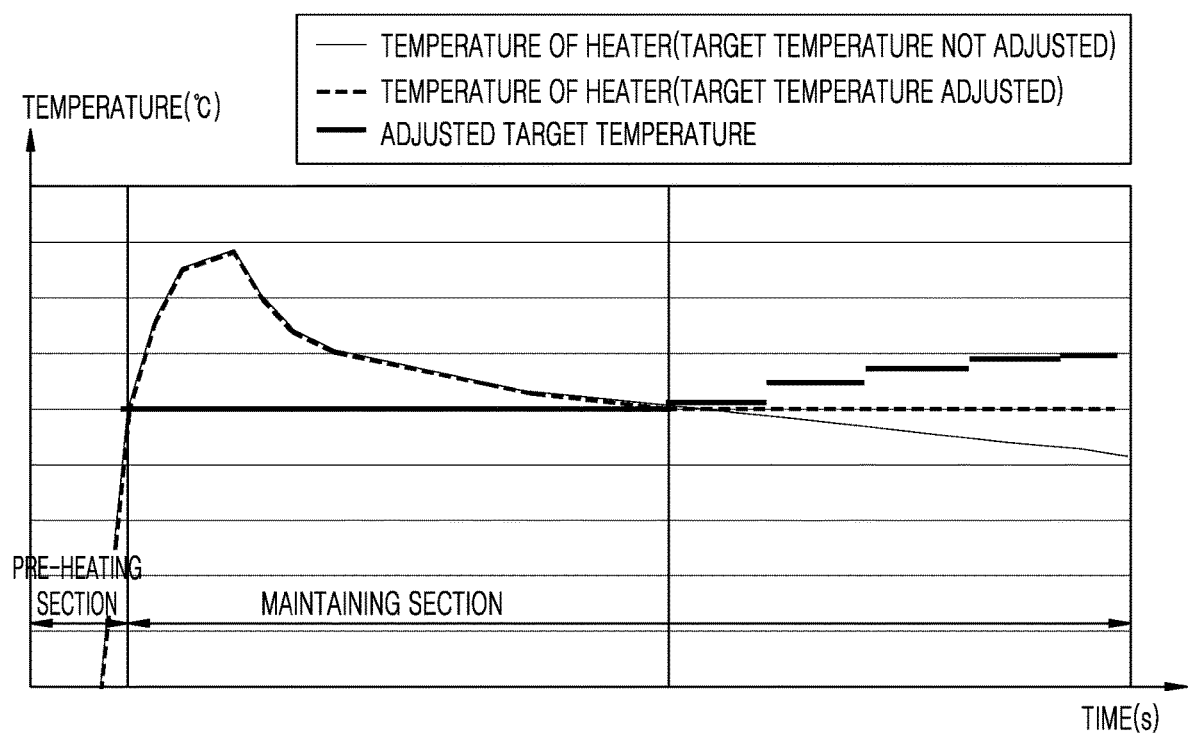
FIG. 19 is a graph illustrating another example of adjusting a target temperature based on a variation in an accumulated value, according to one or more embodiments of the disclosure.

FIG. 19 is a graph illustrating another example of adjusting a target temperature based on a variation in an accumulated value, according to one or more embodiments of the disclosure.

Referring to FIG. 19, another example of adjusting the target temperature based on the variation in the accumulated value is shown. As in the example of FIG. 18, the controller 110 may calculate the accumulated value by accumulating the difference value between the temperature of the heater 130 and the target temperature according to the time lapse, and as shown in FIG. 19, the controller 110 may adjust the target temperature based on the variation in the accumulated value.

However, unlike the example of FIG. 18, in which the controller 110 adjusts the target temperature based on the variation in the accumulated value, the controller 110 may discontinuously adjust the target temperature based on the variation in the accumulated value. Even when the target temperature is discontinuously adjusted, the temperature of the heater 130 may be maintained close to the reference temperature.

The method in which the controller 110 continuously adjusts the target temperature based on the variation in the accumulated value may provide more precise compensation for the temperature of the heater 130, as compared with the method in which the target temperature is discontinuously adjusted. However, when the controller 110 discontinuously adjusts the target temperature based on the variation in the accumulated value, the temperature of the heater 130 may be appropriately compensated for while reducing the calculation amount of the controller 110.

Figure 20:
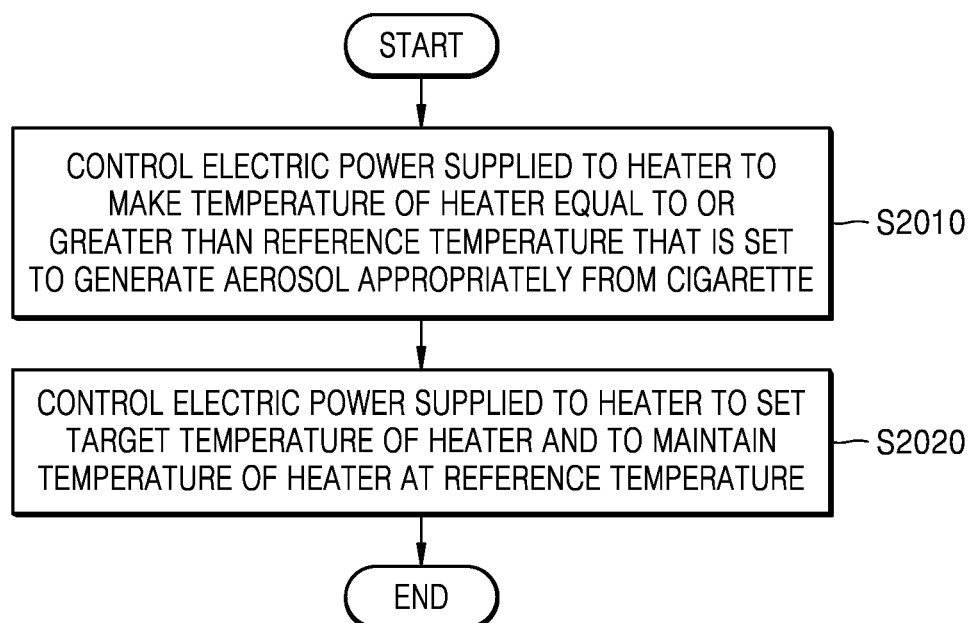
FIG. 20 is a flowchart illustrating a method of controlling a temperature of a heater for heating a cigarette accommodated in an aerosol generator according to one or more embodiments of the disclosure.

FIG. 20 is a flowchart illustrating a method of controlling a temperature of a heater for heating a cigarette accommodated in the aerosol generator according to one or more embodiments of the disclosure.

Referring to FIG. 20, the method of controlling the temperature of the heater for heating the cigarette accommodated in the aerosol generator 10 may include processes that are sequentially processed in the aerosol generator 10 of FIG. 1. Therefore, it will be understood that the descriptions given above with respect to the aerosol generator 10 shown in FIG. 1 also apply to the method of controlling the temperature of the heater for heating the cigarette of FIG. 8, although the descriptions are omitted below.

In operation 52010, the aerosol generator 10 may control the electric power supplied to the heater, so that the temperature of the heater may be equal to or greater than the reference temperature that is suitable for generation of aerosol from the cigarette.

In operation 52020, the aerosol generator 10 may set the target temperature of the heater and control the electric power supplied to the heater so that the temperature of the heater is maintained at the reference temperature. In operation 52020, the aerosol generator 10 may adjust the target temperature in order to compensate for the temperature of the heater when the temperature of the heater decreases below the reference temperature.

One or more of the above embodiments may be embodied in the form of a computer program that may be run in and/or executed by a computer through various elements, and the computer program may be recorded on a non-transitory computer-readable recording medium. Examples of the non-transitory computer-readable recording medium include magnetic media (e.g., hard disks, floppy disks, and magnetic tapes), optical media (e.g., CD-ROMs and DVDs), magneto-optical media (e.g., floptical disks), and hardware devices specifically configured to store and execute program commands (e.g., ROMs, RAMs, and flash memories).

Meanwhile, the computer programs may be specially designed or well known to one of ordinary skill in the computer software field. Examples of the computer programs may include not only machine language code but also high-level language code which is executable by various computing means by using an interpreter.

The particular implementations shown and described herein are illustrative examples of the disclosure and are not intended to otherwise limit the scope of the disclosure in any way. For the sake of brevity, electronics, control systems, software, and other functional aspects of the systems according to the related art may not be described in detail.

Furthermore, the connecting lines or connectors shown in the drawings are intended to represent example functional relationships and/or physical or logical couplings between the various elements. It should be noted that many alternative or additional functional relationships, physical connections, or logical connections may be present in a practical device. Moreover, no item or component is essential to the practice of the present disclosure unless the element is specifically described as "essential" or "critical".

The singular forms "a," "an" and "the" in the specification of the embodiments, in particular, claims, may be intended to include the plural forms as well. Unless otherwise defined, the ranges defined herein is intended to include values within the range as individually applied and may be considered to be the same as individual values constituting the range in the detailed description. Finally, operations constituting methods may be performed in appropriate order unless explicitly described in terms of order or described to the contrary. The present disclosure is not limited to the described order of the steps. The use of any and all examples, or example language (e.g., "such as") provided herein, is intended merely to better illuminate the present disclosure and does not pose a limitation on the scope of the present disclosure unless otherwise claimed. Also, those of ordinary skill in the art will readily appreciate that many alternations, combinations and modifications, may be made according to design conditions and factors within the scope of the appended claims and their equivalents.

INDUSTRIAL APPLICABILITY

An embodiment of the disclosure may be used to produce and implement an electronic cigarette device that provides smoking impression to a user.

What is claimed is:

1. An aerosol generating device comprising:
   a heater configured to generate aerosol by heating an aerosol generating substance; and
   a controller
   configured to:
   control power supplied to the heater such that a temperature of the heater rises to a target temperature,
   measure a first time taken for the temperature of the heater to reach the target temperature,
   calculate a second time such that a ratio of the first time to the second time is smaller than a first preset value, and
   in response to the temperature of the heater exceeding the first target temperature by overshoot, control the power supplied to the heater for the second time such that the temperature of the heater decreases to the target temperature.

2. The aerosol generating device of claim 1, wherein the controller calculates a third time based on the second time, and control the power supplied to the heater for the third time such that the temperature of the heater is maintained at the target temperature.

3. The aerosol generating device of claim 2, wherein the controller calculates the third time such that a ratio of a sum of the first time and the second time to the third time is smaller than a second preset value.

4. The aerosol generating device of claim 3, wherein the second preset value is 1.

5. The aerosol generating device of claim 2, wherein the controller calculates the third time such that a ratio of the second time to the third time is smaller than a second preset value.

6. The aerosol generating device of claim 5, wherein the second preset value is 1.

7. The aerosol generating device of claim 1, wherein the first preset value is 2.

8. The aerosol generating device of claim 1, wherein the controller is further configured to:
   perform pulse width modulation (PWM) control for the first time, and
   perform proportional integral differential (PID) control for the second time.

9. A method of controlling power supplied to a heater, the method comprising:
   controlling the heater to be heated to a target temperature;
   measuring a first time taken for a temperature of the heater to reach the target temperature;
   calculating a second time such that a ratio of the first time to the second time is smaller than a first preset value; and
   in response to the temperature of the heater exceeding the first target temperature by overshoot, controlling the power supplied to the heater for the second time such that the temperature of the heater decreases to the target temperature.

10. The method of claim 9, further comprising:
    calculating a third time based on the second time; and
    controlling the power supplied to the heater for the third time such that the temperature of the heater is maintained at the target temperature.

11. The method of claim 10, wherein a ratio of a sum of the first time and the second time to the third time is smaller than a second preset value.

12. The method of claim 11, wherein the second preset value is 1.

13. The method of claim 10, wherein a ratio of the second time to the third time is smaller than a second preset value.

14. The method of claim 13, wherein the second preset value is 1.

15. The method of claim 9, wherein the first preset value is 2.

16. A computer-readable recording medium having stored thereon a computer program for implementing the method of claim 9.

* * * * *